United States Patent [19]

Imai et al.

[11] Patent Number: 4,746,673
[45] Date of Patent: May 24, 1988

[54] FUNGICIDAL IMIDAZOL-1-YL-CARBOXYLIC ACID ESTER DERIVATIVES

[75] Inventors: Tetsuya Imai, Naruto; Hisashi Takao, Tokushima, both of Japan

[73] Assignee: Otsuka Kagaku Kabushiki Kaisha, Osaka, Japan

[21] Appl. No.: 920

[22] Filed: Jan. 6, 1987

[30] Foreign Application Priority Data

Jan. 16, 1986 [JP] Japan ................................ 61-7731
Feb. 14, 1986 [JP] Japan ................................ 61-31400
Dec. 12, 1986 [JP] Japan ................................ 61-297186

[51] Int. Cl.⁴ .................... A01N 43/50; C07D 233/60
[52] U.S. Cl. ..................................... 514/399; 548/341
[58] Field of Search ........................ 548/341; 514/399

[56] References Cited

U.S. PATENT DOCUMENTS 4,609,669 9/1986 Kume et al. .................... 548/341 X

OTHER PUBLICATIONS

*Chemical Abstracts*, 92:198323y (1980)[Ogata, M., et al., *Chem. Ind.* (London) 1980, (2), 85–86].

*Primary Examiner*—Richard A. Schwartz
*Attorney, Agent, or Firm*—Armstrong, Nikaido, Marmelstein & Kubovcik

[57] ABSTRACT

This invention provides an imidazol-1-yl-carboxylic acid ester derivative represented by the formula

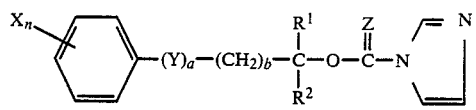

wherein $R^1$ is lower alkyl, cycloalkyl or $R^3(CH_3)_2C$—(wherein $R^3$ is halogenomethyl, acyloxymethyl or alkoxycarbonyl), $R^2$ is a hydrogen atom, lower alkyl or cycloalkyl, X is a hydrogen atom, halogen atom, lower alkyl, cycloalkyl, lower alkenyl, lower alkoxyl, lower alkenyloxy, lower alkynyloxy, lower alkylthio, haloalkyl, haloalkenyl, substituted or unsubstituted phenyl, substituted or unsubstiuted benzyl, substituted or unsubstituted phenoxy, nitro, cyano, —$COR^4$ [ (wherein $R^4$ is lower alkoxyl, lower alkenyloxy, benzyloxy, lower alkylamino or anilino)or

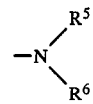

(wherein $R^5$ and $R^6$ are each lower alkyl, acyl, sulfonyl or lower alkoxycarbonyl), n is an integer of from 1 to 3, Y and Z are the same or different and are each an oxygen atom or sulfur atom, a is 0 or 1, and b is 1 or 2, process for preparing the derivative, and a fungicidal composition comprising the derivative as an active component.

8 Claims, No Drawings

FUNGICIDAL IMIDAZOL-1-YL-CARBOXYLIC ACID ESTER DERIVATIVES

The present invention relates to derivatives of imidazol-1-yl-carboxylic acid esters, processes for preparing the same and fungicidal compositions comprising the derivative as an active component.

Known compounds analogous to the imidazol-1-yl-carboxylic acid ester derivatives of the present invention include, for example, benzyl imidazol-1-yl-carboxylate (see Journal of the Organic Chemistry, 47(23), 4471-4477). However, this compound was no fungicidal activity.

An object of the present invention is to provide novel imidazol-1-yl-carboxylic acid ester derivatives having high fungicidal activity.

Another object of the invention is to provide a process for preparing the derivative.

Another object of the invention is to provide fungicidal compositions comprising the derivative as an active component.

Other features of the present invention will become apparent from the following description.

The imidazol-1-yl-carboxylic acid ester derivatives of the present invention are novel compounds which have not been disclosed in literature and are represented by the following formula (I)

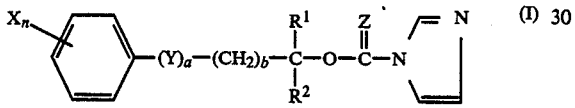

wherein $R^1$ is lower alkyl, cycloalkyl or $R^3(CH_3)_2C-$ (wherein $R^3$ is halogenomethyl, acyloxymethyl or alkoxycarbonyl), $R^2$ is a hydrogen atom, lower alkyl or cycloalkyl, X is a hydrogen atom, halogen atom, lower alkyl, cycloalkyl, lower alkenyl, lower alkoxyl, lower alkenyloxy, lower alkynyloxy, lower alkylthio, haloalkyl, haloalkenyl, substituted or unsubstituted phenyl, substituted or unsubstituted benzyl, substituted or unsubstituted phenoxy, nitro, cyano, $-COR^4$ (wherein $R^4$ is lower alkoxyl, lower alkenyloxy, benzyloxy, lower alkylamino or anilino) or

(wherein $R^5$ and $R^6$ are each lower alkyl, acyl, sulfonyl or lower alkoxycarbonyl), n is an integer of from 1 to 3, Y and Z are the same or different and are each an oxygen atom or sulfur atom, a is 0 or 1, and b is 1 or 2.

Examples of lower alkyl groups in the above formula are methyl, ethyl, n-propyl, isopropyl, n-butyl, isobutyl, sec-butyl, tert-butyl, n-pentyl, isopentyl, sec-pentyl, n-hexyl, isohexyl and like alkyl groups having 1 to 6 carbon atoms.

Examples of cycloalkyl groups are those having 3 to 8 carbon atoms, such as cyclopropyl, cyclopentyl and cyclohexyl.

Examples of halogenomethyl groups are chloromethyl, bromomethyl, fluoromethyl and the like.

Examples of acyloxymethyl groups are acetyloxymethyl, propionyloxymethyl, benzoyloxymethyl, benzoyloxymethyl groups having a halogen atom, $C_{1-3}$ alkyl, $C_{1-3}$ alkoxy or like substituent on the phenyl ring, and the like.

Examples of lower alkoxycarbonyl groups are alkoxycarbonyl groups in which the alkoxy portion has 1 to 6 carbon atoms, such as methoxycarbonyl, ethoxycarbonyl and propyloxycarbonyl.

Examples of halogen atoms include fluorine, chlorine, bromine and iodine atoms.

Examples of lower alkenyl groups are those having 2 to 6 carbon atoms, such as vinyl, propenyl and butenyl.

Examples of lower alkoxyl groups are those having 1 to 6 carbon atoms, such as methoxy, ethoxy, n-propyloxy, isopropyloxy, n-butoxy, isobutyloxy and sec-butyloxy.

Examples of lower alkenyloxy groups are those having 2 to 6 carbon atoms, such as vinyloxy, propenyloxy and butenyloxy.

Examples of lower alkynyloxy groups are those having 2 to 6 carbon atoms, such as ethynyloxy, propynyloxy and butynyloxy.

Examples of lower alkylamino groups are mono- and di-alkylamino groups having 1 to 6 carbon atoms, such as monomethylamino, monoethylamino, monopropylamino, dimethylamino, diethylamino and dipropylamino.

Examples of acyl groups are acetyl, propionyl, benzoyl and benzoyl groups having a halogen atom, $C_{1-3}$ alkyl, $C_{1-3}$ alkoxy or like substituent on the phenyl ring.

Examples of sulfonyl groups are methylsulfonyl, ethylsulfonyl, benzenesulfonyl and benzenesulfonyl groups having a halogen atom, $C_{1-3}$ alkyl, $C_{1-3}$ alkoxy or like substituent on the phenyl ring.

Examples of lower alkylthio groups are alkylthio groups having 1 to 6 carbon atoms, such as methylthio, ethylthio, propylthio and butylthio.

Examples of haloalkyl groups are alkyl groups having 1 to 6 carbon atoms and substituted with at least one halogen atom, such as monochloromethyl, dichloromethyl, trichloromethyl, monobromomethyl, dibromomethyl, monofluoromethyl, difluoromethyl, trifluoromethyl, 1,2-dichloroethyl, 1,2-dibromoethyl, 1,1,2-trichloroethyl and monofluoroethyl.

Examples of haloalkenyl groups are alkenyl groups having 2 to 6 carbon atoms and substituted with halogen atoms, such as 2,2-dichlorovinyl and 2,2-dibromovinyl.

Examples of substituents on the phenyl ring of phenyl, benzyl and phenoxy groups are the above-mentioned halogen atoms, lower alkyl groups, lower alkoxy groups, nitro group, cyano group, etc.

The compounds of the present invention represented by the formula (I) are useful as agricultural and horticultural fungicides as will be described below.

The compounds of the invention, which can be prepared by various processes, are prepared easily generally by the process represented by Reaction Formula-1 or Reaction Formula-2 given below.

Reaction Formula-1

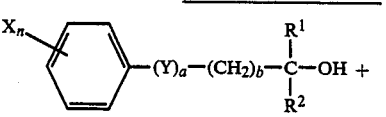

(II)

-continued
Reaction Formula-1

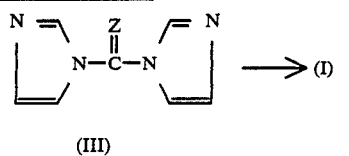

wherein $R^1$, $R^2$, X, n, Y, Z, a and b are as defined above.

Reaction Formula-2

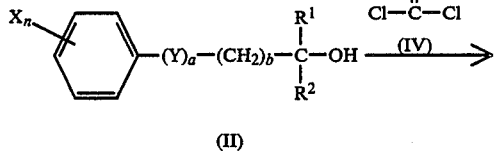

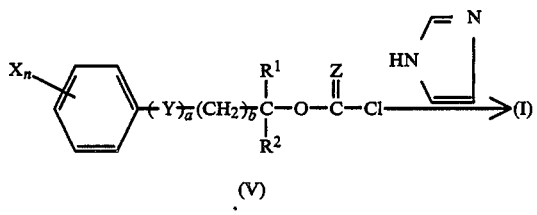

wherein $R^1$, $R^2$, X, n, Y, Z, a and b are as defined above.

According to Reaction Formula-1, the compound of the invention is prepared by reacting a carbinol derivative of the formula (II) with an N,N'-carbonyldiimidazole of the formula (III). This reaction is conducted in a suitable solvent or without using any solvent. Examples of useful solvents are ethers such as diethyl ether, dibutyl ether, tetrahydrofuran and dioxane, hydrocarbon halides such as methylene chloride, chloroform and dichloroethane, ketones such as acetone, methyl ethyl ketone, methyl isopropyl ketone and cyclohexanone, aromatic hydrocarbons such as benzene, toluene and xylene, ethyl acetate, acetonitrile, dimethylformamide, dimethyl sulfoxide, etc. and mixtures of such solvents. Although the proportions of the compound of the formula (II) and the compound of the formula (III) are not limited specifically, usually about 0.5 to about 2 moles, preferably about 0.7 to about 1.5 moles, of the latter is used per mole of the former. The reaction, which can be carried out either at room temperature or with heating, proceeds suitably usually at room temperature to around the boiling point of the solvent used and takes generally about 1 to about 10 hours.

According to Reaction Formula-2, the compound of the present invention is prepared by reacting a carbinol derivative of the formula (II) with a compound of the formula (IV) and subsequently reacting imidazole with the resulting compound of the formula (V).

These reactions are conducted in a suitable solvent or in the absence of solvent. Examples of useful solvents are ethers such as diethyl ether, dibutyl ether, tetrahydrofuran and dioxane, hydrocarbon halides such as methylene chloride, chloroform, dichloroethane and carbon tetrachloride, aromatic hydrocarbons such as benzene, toluene and xylene, ethyl acetate, dimethylformamide, dimethyl sulfoxide, pyridine, etc. and mixtures of such solvents.

In reacting the compound of the formula (II) with the compound of the formula (IV), the compound of the formula (IV) is used in the form of a gas or liquid, or a solution of the latter in such a solvent is added dropwise to the former. According to the present invention, a compound producing the compound of the formula (IV) is usable in place of the compound (IV). Any of known compounds, such as trichloromethyl chloroformate, is usable insofar as it is capable of producing the compound of the formula (IV) under the reaction conditions. The proportions of the compound of the formula (II) and the compound of the formula (IV) are not limited specifically, but it is preferable to use about 0.5 to about 5 moles, more preferably about 1 to about 3 moles, of the latter per mole of the former. Preferably, the reaction system contains a basic compound. Any of various known basic compounds, such as triethylamine, tributylamine, dimethylaniline, diethylaniline and pyridine, is usable insofar as the compound is capable of capturing the hydrogen chloride resulting from the reaction. Such a basic compound is used in an amount usually of about 0.5 to about 5 moles, preferably about 1 to about 3 moles, per mole of the compound of the formula (II). The reaction, which can be conducted either at room temperature or with cooling, usually proceeds favorably at about $-10°$ C. to room temperature and generally takes about 1 to about 15 hours.

The compound of the formula (V) thus produced is used, as isolated or as it is without isolation, for the subsequent reaction.

In reacting imidazole with the compound (V) resulting from the above reaction, the proportions of these two compounds are not limited specifically, but it is usually preferable to use about 0.5 to about 2 moles, more preferably about 0.7 to about 1.5 moles, of imidazole per mole of the compound (V). It is desirable that a basic compound, such as those mentioned above, be also present in the system for this reaction. The basic compound is used usually in an amount of about 0.5 to about 2 moles, preferably about 0.7 to about 1.5 moles, per mole of the compound of the formula (V). The reaction, which can be carried out either at room temperature or with heating, favorably proceeds usually at room temperature to around the boiling point of the solvent used and generally takes about 1 to about 10 hours.

With reference to Reaction Formulae-1 and -2, the compound of the formula (II) to be used as a starting material is easily prepared by a known process, for example, by the process represented by Reaction Formula-3, -4 or -5.

Reaction Formula-3

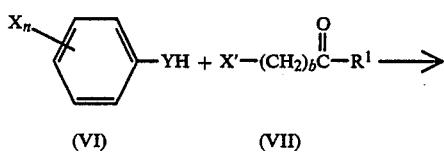

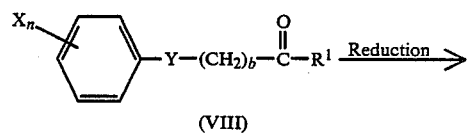

-continued
Reaction Formula-3

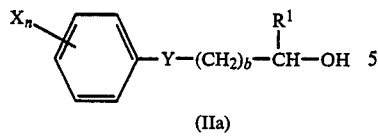

(IIa)

wherein R¹, X, n, Y and b are as defined above, and X' is a halogen atom.

With reference to Reaction Formula-3, the reaction of the compound of the formula (VI) with the compound of the formula (VII) is conducted in water or in an organic solvent. Examples of useful solvents are ethers such as diethyl ether, dibutyl ether, tetrahydrofuran and dioxane, hydrocarbon halides such as methylene chloride, chloroform and dichloroethane, aromatic hydrocarbons such as benzene, toluene and xylene, ketones such as acetone, methyl ethyl ketone and cyclohexanone, acetonitrile, dimethylformamide, dimethyl sulfoxide and the like. Although the proportions of the compound (VI) and the compound (VII) to be used are not limited specifically, usually about 0.5 to about 2 moles, preferably about 1 to about 1.5 moles, of the latter is used per mole of the former. For the reaction, a basic agent is used, or the phenolic compound represented by the formula (VI) is used in the form of a sodium salt or potassium salt. Examples of useful basic agents are alkali carbonates such as sodium carbonate and potassium carbonate, alkali hydroxides such as sodium hydroxide and potassium hydroxide, metallic sodium, sodium methylate, sodium hydride and the like. The reaction is carried out usually at a temperature of about 50° to about 150° C. and generally takes about 5 to 15 hours.

With the reference to Reaction Formula-3, the reaction wherein the compound of the formula (VIII) is reduced to the compound of the formula (IIa) can be carried out by various processes such as a catalytic reduction process and a process employing a reducing agent. For example, when the catalytic reduction process is resorted to, the compound (VIII) is hydrogenated in a solvent such as methanol, ethanol or like alcohol or acetonitrile, using a catalyst such as noble metal, noble metal oxide or Raney catalyst. Among such catalysts, platinum, platinum oxide and nickel are preferred. While the reaction can be conducted at a suitable temperature within a wide range, the preferred temperature is about 20° to 50° C. The reaction can be carried out at atmospheric pressure or increased pressure. When the process employing a reducing agent is resorted to, the reaction is conducted using a catalyst such as aluminum isopropylate or sodium borohydride and a solvent such as methanol, ethanol or like alcohol or diethyl ether, tetrahydrofuran or like ether. The catalyst is used usually in an amount of about 0.1 to about 2 moles, preferably about 0.5 to about 1.5 moles, per mole of the compound of the formula (VIII). The reaction temperature is usually in the range of 0° to 100° C.

Reaction Formula-4

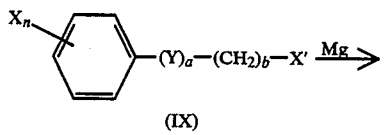

(IX)

-continued
Reaction Formula-4

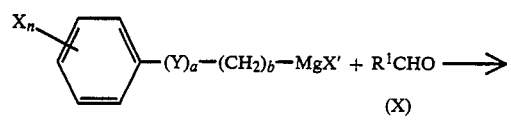

(X)

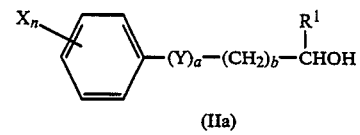

(IIa)

Reaction Formula-5

$R^2X' \xrightarrow{Mg} R^2MgX' +$ (XI)

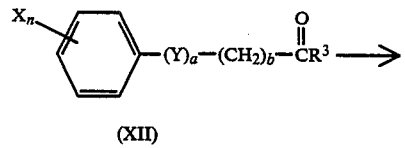

(XII)

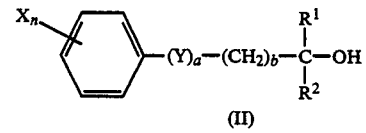

(II)

wherein R¹, R², X, Y, n, a and b are as defined above, X' is a halogen atom, and R³ is the same as R¹ or lower alkoxyl.

The reaction represented by Reaction Formula-4 or -5, which is the common Grignard Reaction, is conducted in an ether solvent such as diethyl ether, dibutyl ether or tetrahydrofuran. Although the proportions of a halide of the formula (IX) or (XI) and magnesium to be reacted therewith are not limited specifically, it is usually desirable to use 0.5 to 1.5 moles, more desirably 0.8 to 1.2 moles, of the latter per mole of the former. The reaction proceeds favorably at 0° C. to around the boiling point of the solvent and generally takes about 1 to about 10 hours. The resulting Grignard reagent is subsequently reacted as it is with an aldehyde, ketone or carboxylic acid ester derivative represented by the formula (X) or (XII). The compound of the formula (X) or (XII) is used usually in an amount of about 0.1 to about 3 moles, preferably about 0.5 to about 2.5 moles, per mole of the halide of the formula (IX) or (XI). This reaction proceeds favorably at about 0° about 50° C. and generally takes about 0.5 to about 3 hours.

The compound of the present invention obtained by the foregoing processes can be easily isolated from the reaction mixture and purified by a usual method such as solvent extraction, solvent dilution method, recrystallization or column chromatography, whereby the desired compound can be prepared with a high purity.

The compound of the invention is characterized by high fungicidal activity and a wide activity spectrum. The present compound exhibits outstanding fungicidal activity on various pathogens, for example, of powdery mildew, scab, smut, gray mold, anthracnose, blast, leaf spots (caused by helminthosporia), sheath blight, etc. Moreover, the compound of the invention exhibits no phytotoxicity at a concentration required for controlling these pathogens and is low in toxicity to warm-blooded animals. Accordingly, the present compound is effectively usable for preventing diseases of agricultural plants such as vegetables, fruit trees, rice and mulberry trees.

For use an a fungicide, the compound of the invention may be used as it is, while it is generally used as admixed with auxiliary agents which are commonly used for formulating agricultural chemical preparations. Thus, the compound is formulated into a composition which is not limited in type. Suitably, the composition is in the form of a powder, emulsifiable concentrate, granules, wettable powder or flowable concentrate. Useful auxiliary agents are a wide variety of those commonly used in the art and including, for example, extenders such as kieselguhr, kaolin, clay, bentonite, white carbon and talc, surfactants such as polyoxyethylene alkyl ether, polyoxyethylene alkyl phenyl ether, polyoxyethylene sorbitan fatty acid ester, polyoxyethylene fatty acid ester, sodium alkylbenzenesulfonate, sodium lignosulfonate, sodium alkylsulfate, sodium polyoxyethylenealkylsulfate and salt of naphthalenesulfonic acid-formalin condensation product, organic solvents such as benzene, toluene, xylene, acetone, cyclohexanone, methanol, ethanol, isopropyl, alcohol, dioxane, dimethylformamide, dimethyl sulfoxide and carbon tetrachloride, etc.

Although the amount of the present compound to be incorporated into the fungicidal composition of the invention is not limited specifically, it is desirable to suitably admix auxiliary agents with the compound so that the composition contains usually about 0.1 to about 90 wt.%, preferably about 1 to about 70 wt.%, of the active component.

The present fungicidal composition may be used as it is without dilution or as diluted to about 500- to about 10,000-fold. Although the suitable dosage can not be determined specifically but varies with the type of composition, method and timing of application, kind of disease to be treated, etc., it is desirable to use about 5 to about 200 g/10a of the composition calculated as the active component.

The present invention will be described in greater detail with reference to the following reference examples, examples, formulation examples and test examples.

REFERENCE EXAMPLE 1

Preparation of
1-(p-chlorophenoxy)-3,3-dimethyl-2-butanone

A 12.8 g quantity of p-chlorophenol, 13.4 g of 1-chloro-3,3-dimethyl-2-butanone, 13.8 g of anhydrous potassium carbonate and 100 ml of acetonitrile were placed into a 200-ml egg plant type flask and refluxed for 8 hours. The resulting potassium chloride was filtered off from the reaction mixture, and the filtrate was concentrated in a vacuum to obtain crude crystals, which were recrystallized from n-hexane, giving 16.0 g of the above-identified desired compound, m.p. 62°-63° C.

REFERENCE EXAMPLE 2

Preparation of
1-(p-chlorophenoxy)-3,3-dimethyl-2-butanol

Into a 200-ml egg plant type flask were placed 9.0 g of 1-(p-chlorophenoxy)-3,3-dimethyl-2-butanone and 80 ml of methanol, and 0.8 g of sodium borohydride was further placed into the flask with cooling and stirring. After stirring the mixture at room temperature for 1 hour, the reaction mixture was concentrated in a vacuum, and 50 ml of water was added to the resulting residue, followed by extraction with 30 ml of ether twice. The combined ethereal extract was washed with saturated aqueous sodium chloride solution, dried over anhydrous magnesium sulfate and concentrated in a vacuum. The residue was purified by silica gel column chromatography, giving 8.5 g of the above-identified desired compound.

REFERENCE EXAMPLE 3

Preparation of
1-(p-chlorophenyl)-3,3-dimethyl-2-butanol

A 10 ml quantity of ether solution of 4.3 g of (0.05 mole) of pivalaldehyde was added dropwise to a solution of p-chlorobenzylmagnesium chloride (0.055 mole) in 100 ml of ether with cooling and stirring. The mixture was thereafter stirred at room temperature for 1 hour and then placed into 5% aqueous solution of hydrochloride acid containing pieces of ice. After separating off the oily layer, the aqueous layer was subjected to extraction with ether. The ethereal extract and the oily layer were combined together, washed with saturated sodium chloride aqueous solution, dried over anhydrous magnesium sulfate and distilled to remove the solvent, affording 10.5 g of the above-identified desired compound in the form of a white solid.

REFERENCE EXAMPLE 4

Preparation of
1-(p-chlorophenoxy)-3,3-dimethyl-4-chloro-2-butanone

Into a 100-ml egg plant type flask were placed 2.4 g of 1-(p-chlorophenoxy)-3,3-dimethyl-4-hydroxy-2-butanone, 2.6 g of triphenylphosphine and 50 ml of carbon tetrachloride, which were then refluxed for 18 hours. The reaction mixture was cooled, the crystals separating out were filtered off, and the filtrate was concentrated in a vacuum. The residue obtained was purified by silica gel column chromatography, giving 1.8 g of the above-identified desired compound.

REFERENCE EXAMPLE 5

Preparation of
1-(p-chlorophenoxy)-3,3-dimethyl-4-chloro-2-butanol

Into a 100-ml egg plant type flask were placed 2.6 g of 1-(p-chlorophenoxy)-3,3-dimethyl-4-chloro-2-butanone and 40 ml of methanol, and 0.2 g of sodium borohydride was further placed into the flask with cooling and stirring. After stirring the mixture at room temperature for 1 hour, the reaction mixture was concentrated in a vacuum, and 50 ml of water was added to the resulting residue, followed by extraction with 30 ml of ether twice. The combined ethereal extract was washed with saturated aqueous sodium chloride solution, dried over anhydrous magnesium sulfate and concentrated in a vacuum. The residue obtained was purified by silica gel column chromatography, giving 2.3 g of the above-identified desired compound.

REFERENCE EXAMPLE 6

Preparation of
1-(p-chlorophenylthio)-3,3-dimethyl-2-butanone

A 14.45 g quantity of p-chlorothiophenol and 13.8 g of anhydrous potassium carbonate were added to 200 ml of acetonitrile, and 13.45 of 1-chloro-3,3-dimethyl-2-butanone was added in small portions to the mixture while stirring the mixture. After stirring the mixture at 70° to 75° C. for 6 hours, the solid separating out was filtered off. The filtrate was concentrated to obtain a residue, which was subjected to extraction with benzene. To the extract was added 200 ml of 10% sodium hydroxide solution, followed by stirring at room temperature for 1 hour. The benzene layer was separated off, washed with water, then dried over anhydrous magnesium sulfate and distilled in a vacuum to remove the solvent, giving 20.2 g of the above-identified desired compound in the form of a pale yellow oil.

REFERENCE EXAMPLE 7

Preparation of 1-(p-chlorophenylthio)-3,3-dimethyl-2-butanol

A 0.4 g quantity of sodium borohydride was added in small portions to a solution of 2.43 g of 1-(p-chlorophenylthio)-3,3-dimethyl-2-butanone in 50 ml of methanol at a temperature of up to 10° C. with stirring. After the completion of addition, the mixture was stirred at room temperature for 30 minutes and then distilled in a vacuum to remove the methanol. The residue was subjected to extraction with ether. The extract was washed with water, then dried over anhydrous magnesium sulfate and distilled to remove the solvent, affording 2.4 g of the above-identified desired compound in the form of a colorless oil.

REFERENCE EXAMPLE 8

Preparation of 1-(p-chlorophenoxy)-2-methyl-2-propanol

To 100 ml of ether solution of 24 g of methylmagnesium bromide was added dropwise 30 ml of ether solution of 10.7 g of ethyl p-chlorophenoxyacetate at a temperature of up to 10° C. with stirring. The mixture was thereafter stirred at room temperature for 1 hour and then placed into 10% aqueous hydrochloric acid solution with ice cooling. The oily layer was subjected to extraction with ether, and the extract was washed with saturated aqueous sodium chloride solution, dried over anhydrous magnesium sulfate and distilled to remove the solvent, giving 8.9 g of the above-identified desired compound in the form of a colorless oil.

REFERENCE EXAMPLE 9

Preparation of 1-(p-chlorophenoxy)-2,3-dimethyl-2-butanol

To 50 ml of ether solution of 12 g of methylmagnesium bromide was added dropwise in small portions 30 ml of ether solution of 10.6 g of p-chlorophenoxy methyl isopropyl ketone at a temperature of up to 10° C. with stirring. The mixture was thereafter stirred at room temperature for 1 hour and then placed into 100 ml of 10% aqueous solution of hydrochloric acid with ice cooling. The ethereal layer was separated off, washed with saturated aqueous solution of sodium chloride, dried over anhydrous magnesium sulfate and distilled to remove the solvent, affording 9.1 g of the above-identified desired compound in the form of a pale yellow oil.

EXAMPLE 1

Preparation of 1'-(m-chlorophenoxy)-3',3'-dimethyl-2'-butyl imidazol-1-yl-carboxylate A 1.6 g quantity of 1-(m-chlorophenoxy)-3,3-dimethyl-2-butanol, 1.4 g of N,N'-carbonyldiimidazole and 40 ml of ethyl acetate were placed into a 100-ml egg plant type flask and refluxed for 3 hours. The reaction mixture was concentrated in a vacuum, and the resulting residue was purified by silica gel column chromatography, giving 1.6 g of the above-identified desired compound.

M.p.: 67°–68° C.

| Elementary analysis: | C | H | N |
|---|---|---|---|
| Calcd. for $C_{16}H_{19}N_2O_3Cl$ (%) | 59.54 | 5.93 | 8.68 |
| Found (%) | 59.01 | 5.88 | 8.81 |

NMR spectrum (CDCl$_3$) δ ppm: 1.10 (9H), 4.10 (2H), 5.15 (1H), 6.50–7.10 (5H), 7.25 (1H), 7.98 (1H).

These results indicated that the compound obtained was

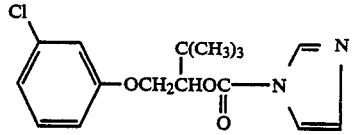

EXAMPLE 2

Preparation of 1'-(o-chlorophenoxy)-3',3'-dimethyl-2'-butyl imidazol-1-yl-carboxylate A 2.3 g quantity of 1-(o-chlorophenoxy)-3,3-dimethyl-2-butanol, 0.81 ml of pyridine and 50 ml of ethyl acetate was placed into a 100-ml four-necked flask, and 0.6 ml of trichloromethyl chloroformate was added dropwise to the mixture with cooling and stirring. The mixture was thereafter stirred at room temperature for 15 hours and then cooled again. To the mixture were added 0.7 g of imidazole and 0.81 ml of pyridine, and the resulting mixture was stirred at room temperature for 30 minutes and further refluxed for 3 hours. The reaction mixture was washed with water and saturated aqueous solution of sodium chloride, dried over anhydrous magnesium sulfate and concentrated in a vacuum. The residue obtained was purified by silica gel column chromatography, giving 1.5 g of the above-identified desired compound.

M.p.: 123°–124° C.

| Elementary analysis: | C | H | N |
|---|---|---|---|
| Calcd. for $C_{16}H_{19}N_2O_3Cl$ (%) | 59.54 | 5.93 | 8.68 |
| Found (%) | 58.98 | 5.90 | 8.75 |

NMR spectrum (CDCl$_3$) δ ppm: 1.10 (9H), 4.10 (2H), 5.17 (1H), 6.60–7.20 (5H), 7.28 (1H), 8.00 (1H).

These results indicated that the compound obtained was

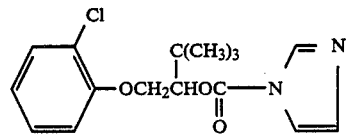

EXAMPLES 3-69

The compounds listed in Table 1 below were prepared in the same manner as in Example 1 or 2 using suitable starting materials.

TABLE 1

| Ex. No. | Formula | Property | NMR spectrum (CDCl₃) δ ppm |
|---|---|---|---|
| 3 | (phenyl)-OCH₂CHOCON(imidazolyl), C(CH₃)₃ | m.p. 71–72° C. | 1.05 (9H), 4.10 (2H), 5.17 (1H), 5.17 (1H), 6.60–7.20 (6H), 7.29 (1H), 8.00 (1H) |
| 4 | 4-F-C₆H₄-OCH₂CHOCON(imidazolyl), C(CH₃)₃ | m.p. 45–46° C. | 1.10 (9H), 4.10 (2H), 5.15 (1H), 6.65–6.85 (4H), 6.95 (1H), 7.28 (1H), 8.00 (1H) |
| 5 | 4-Cl-C₆H₄-OCH₂CHOCON(imidazolyl), C(CH₃)₃ | m.p. 52–53° C. | 1.07 (9H), 4.10 (2H), 5.13 (1H), 6.60 (2H), 6.90 (1H), 7.04 (2H), 7.25 (1H), 7.96 (1H) |
| 6 | 4-Br-C₆H₄-OCH₂CHOCON(imidazolyl), C(CH₃)₃ | m.p. 67–68° C. | 1.05 (9H), 4.10 (2H), 5.15 (1H), 6.56 (2H), 6.91 (1H), 7.17 (1H), 7.27 (1H), 7.98 (1H) |
| 7 | 2-Br-C₆H₄-OCH₂CHOCON(imidazolyl), C(CH₃)₃ | m.p. 116–117° C. | 1.05 (9H), 4.15 (2H), 5.21 (1H), 6.50–7.35 (6H), 8.00 (1H) |
| 8 | 4-O₂N-C₆H₄-OCH₂CHOCON(imidazolyl), C(CH₃)₃ | m.p. 125–126° C. | 1.10 (9H), 4.25 (2H), 5.20 (1H), 6.78 (2H), 6.92 (1H), 7.30 (1H), 8.00 (3H) |
| 9 | 4-NC-C₆H₄-OCH₂CHOCON(imidazolyl), C(CH₃)₃ | m.p. 110–111° C. | 1.10 (9H), 4.20 (2H), 5.20 (1H), 6.82 (2H), 6.95 (1H), 7.30 (1H), 7.41 (2H), 8.00 (1H) |
| 10 | Cl₂C=CH-C₆H₄-OCH₂CHOCON(imidazolyl), C(CH₃)₃ | m.p. 83–84° C. | 1.10 (9H), 4.17 (2H), 5.18 (1H), 6.60 (1H), 6.71 (2H), 6.93 (1H), 7.30 (3H), 8.00 (1H) |
| 11 | (CH₃)₂CH-C₆H₄-OCH₂CHOCON(imidazolyl), C(CH₃)₃ | m.p. 72–73° C. | 1.05 (9H), 1.16 (6H), 2.75 (1H), 4.15 (2H), 5.15 (1H), 6.60 (2H), 6.90 (1H), 6.95 (2H), 7.23 (1H), 7.95 (1H) |
| 12 | CH₃-C₆H₄-OCH₂CHOCON(imidazolyl), C(CH₃)₃ | m.p. 80–81° C. | 1.05 (9H), 2.17 (3H), 4.10 (2H), 5.12 (1H), 6.58 (2H), 6.88 (3H), 7.25 (1H), 7.98 (1H) |
| 13 | (biphenyl)-OCH₂CHOCON(imidazolyl), C(CH₃)₃ | m.p. 90–91° C. | 1.05 (9H), (9H), 4.15 (2H), 5.15 (1H), 6.73 (2H), 6.90 (1H), 7.10–7.40 (8H), 7.98 (1H) |

TABLE 1-continued

| Ex. No. | Formula | Property | NMR spectrum (CDCl₃) δ ppm |
|---|---|---|---|
| 14 | (CH₃)₃C—⟨C₆H₄⟩—OCH₂CHOCON(pyrrole), with C(CH₃)₃ branch | m.p. 109–110° C. | 1.05 (9H), 1.23 (9H), 4.10 (2H), 5.15 (1H), 6.62 (2H), 6.90 (1H), 7.12 (2H), 7.25 (1H), 7.98 (1H) |
| 15 | 3-CH₃-C₆H₄—OCH₂CHOCON(pyrrole), C(CH₃)₃ | m.p. 72–73° C. | 1.05 (9H), 2.23 (3H), 4.13 (2H), 5.15 (1H), 6.40–6.70 (3H), 6.90 (2H), 7.25 (1H), 8.00 (1H) |
| 16 | C₆H₅CH₂—C₆H₄—OCH₂CHOCON(pyrrole), C(CH₃)₃ | m.p. 70–71° C. | 1.05 (9H), 3.80 (2H), 4.13 (2H), 5.15 (1H), 6.60–7.30 (9H), 6.90 (1H), 7.30 (1H), 8.00 (1H) |
| 17 | C₂H₅—C₆H₄—OCH₂CHOCON(pyrrole), C(CH₃)₃ | m.p. 69–70° C. | 1.05 (9H), 1.15 (3H), 2.50 (2H), 4.12 (2H), 5.15 (1H), 6.62 (2H), 6.92 (3H), 7.25 (1H), 7.98 (1H) |
| 18 | n-C₃H₇—C₆H₄—OCH₂CHOCON(pyrrole), C(CH₃)₃ | m.p. 66–67° C. | 0.88 (3H), 1.05 (9H), 1.60 (2H), 2.50 (2H), 4.10 (2H), 5.15 (1H), 6.60 (2H), 6.90 (3H), 7.25 (1H), 7.98 (1H) |
| 19 | n-C₄H₉—C₆H₄—OCH₂CHOCON(pyrrole), C(CH₃)₃ | m.p. 73–74° C. | 0.88 (3H), 1.05 (9H), 1.20–1.70 (4H), 2.50 (2H), 4.10 (2H), 5.15 (1H), 6.60 (2H), 6.90 (3H), 7.25 (1H), 7.96 (2H) |
| 20 | sec-C₄H₉—C₆H₄—OCH₂CHOCON(pyrrole), C(CH₃)₃ | m.p. 100–101° C. | 0.77 (3H), 1.05 (9H), 1.15 (3H), 1.50 (2H), 2.45 (1H), 4.10 (2H), 5.15 (1H), 6.62 (2H), 6.90 (3H), 7.25 (1H), 7.98 (1H) |
| 21 | cyclohexyl—C₆H₄—OCH₂CHOCON(pyrrole), C(CH₃)₃ | m.p. 96–97° C. | 1.05 (9H), 1.10–1.90 (11H), 4.10 (2H), 5.15 (1H), 6.60 (2H), 6.90 (3H), 7.25 (1H), 7.95 (1H) |
| 22 | CH₃O—C₆H₄—OCH₂CHOCON(pyrrole), C(CH₃)₃ | m.p. 77–78° C. | 1.05 (9H), 3.62 (3H), 4.10 (2H), 5.15 (1H), 6.63 (4H), 6.90 (1H), 7.27 (1H), 7.98 (1H) |
| 23 | CH₃S—C₆H₄—OCH₂CHOCON(pyrrole), C(CH₃)₃ | m.p. 69–70° C. | 1.05 (9H), 2.35 (3H), 4.10 (2H), 5.15 (1H), 6.65 (2H), 6.90 (1H), 7.07 (2H), 7.25 (1H), 6.98 (1H) |
| 24 | 3-CH₃O-C₆H₄—OCH₂CHOCON(pyrrole), C(CH₃)₃ | m.p. 57–58° C. | 1.05 (9H), 3.62 (3H), 4.10 (2H), 5.13 (1H), 6.20–6.45 (3H), 6.90 (2H), 7.27 (1H), 7.98 (1H) |
| 25 | 2-OCH₃-C₆H₄—OCH₂CHOCON(pyrrole), C(CH₃)₃ | m.p. 66–67° C. | 1.05 (9H), 3.52 (3H), 4.15 (2H), 5.15 (1H), 6.70 (4H), 6.90 (1H), 7.25 (1H), 7.95 (1H) |

TABLE 1-continued

| Ex. No. | Formula | Property | NMR spectrum (CDCl$_3$) δ ppm |
|---|---|---|---|
| 26 | C$_2$H$_5$O-C$_6$H$_4$-OCH$_2$CH(C(CH$_3$)$_3$)OCON(pyrrolyl) | m.p. 88–89° C. | 1.05 (9H), 1.32 (3H), 3.83 (2H), 4.10 (2H), 5.10 (1H), 6.60 (4H), 6.90 (1H), 7.23 (1H), 7.95 (1H) |
| 27 | 4-Cl-C$_6$H$_4$-O-C$_6$H$_4$-OCH$_2$CH(C(CH$_3$)$_3$)OCON(pyrrolyl) | m.p. 62–63° C. | 1.07 (9H), 4.10 (2H), 5.15 (1H), 6.65 (2H), 6.70 (4H), 6.90 (1H), 7.05 (2H), 7.25 (1H), 7.98 (1H) |
| 28 | 2,4-Cl$_2$-C$_6$H$_3$-O-C$_6$H$_4$-OCH$_2$CH(C(CH$_3$)$_3$)OCON(pyrrolyl) | — | 1.05 (9H), 4.12 (2H), 5.15 (1H), 6.60 (1H), 6.70 (4H), 6.90 (2H), 7.30 (1H), 8.00 (1H) |
| 29 | 2,4-Cl$_2$-C$_6$H$_3$-OCH$_2$CH(C(CH$_3$)$_3$)OCON(pyrrolyl) | — | 1.10 (9H), 4.15 (2H), 5.20 (1H), 6.67 (1H), 6.92 (2H), 7.15 (1H), 7.30 (1H), 8.00 (1H) |
| 30 | 2,4-(CH$_3$)$_2$-C$_6$H$_3$-OCH$_2$CH(C(CH$_3$)$_3$)OCON(pyrrolyl) | m.p. 67–68° C. | 1.05 (9H), 1.97 (3H), 2.10 (3H), 4.05 (2H), 5.15 (1H), 6.48 (1H), 6.70 (2H), 6.90 (1H), 7.25 (1H), 7.98 (1H) |
| 31 | 2-CH$_3$-4-Cl-C$_6$H$_3$-OCH$_2$CH(C(CH$_3$)$_3$)OCON(pyrrolyl) | m.p. 83–84° C. | 1.07 (9H), 1.95 (3H), 4.05 (2H), 5.15 (1H), 6.50 (1H), 6.90 (3H), 7.28 (1H), 8.00 (1H) |
| 32 | n-C$_3$H$_7$O-C$_6$H$_4$-OCH$_2$CH(C(CH$_3$)$_3$)OCON(pyrrolyl) | m.p. 54.8° C. | 0.97 (3H), 1.06 (9H), 1.72 (2H), 3.35 (2H), 4.10 (2H), 5.12 (1H), 6.62 (4H), 6.97 (1H), 7.19 (1H), 7.98 (1H) |
| 33 | 2,6-Cl$_2$-C$_6$H$_3$-OCH$_2$CH(C(CH$_3$)$_3$)OCON(pyrrolyl) | m.p. 98–99° C. | 1.10 (9H), 4.10 (2H), 5.20 (1H), 6.81 (1H), 6.88 (1H), 7.05 (2H), 7.30 (1H), 8.00 (1H) |
| 34 | Cl$_2$C=CH-C$_6$H$_3$(Cl)-OCH$_2$CH(C(CH$_3$)$_3$)OCON(pyrrolyl) | m.p. 102–103° C. | 1.05 (9H), 4.15 (2H), 5.17 (1H), 6.50 (1H), 6.70 (1H), 6.90 (1H), 6.98 (1H), 7.30 (3H) |
| 35 | 3,4-(CH$_3$O)$_2$-C$_6$H$_3$-OCH$_2$CH(C(CH$_3$)$_3$)OCON(pyrrolyl) | m.p. 59–60° C. | 1.07 (9H), 3.70 (6H), 4.10 (2H), 5.12 (1H), 6.20 (1H), 6.28 (1H), 6.58 (1H), 6.90 (1H), 6.95 (1H), 7.25 (1H) |
| 36 | 3,5-Cl$_2$-C$_6$H$_3$-OCH$_2$CH(C(CH$_3$)$_3$)OCON(pyrrolyl) | m.p. 95–96° C. | 1.05 (9H), 4.10 (2H), 5.12 (1H), 6.60 (2H), 6.80 (1H), 6.90 (1H), 7.28 (1H), 7.98 (1H) |

TABLE 1-continued

| Ex. No. | Formula | Property | NMR spectrum (CDCl₃) δ ppm |
|---|---|---|---|
| 37 | 3,4-(CH₃)₂-C₆H₃-OCH₂CH(C(CH₃)₃)COCON-pyrrole | m.p. 102–103° C. | 1.05 (9H), 2.10 (6H), 4.10 (2H), 5.10 (1H), 6.40 (1H), 6.50 (1H), 6.80 (1H), 6.90 (1H), 7.20 (1H), 7.93 (1H) |
| 38 | 2,4,6-Cl₃-C₆H₂-OCH₂CH(C(CH₃)₃)COCON-pyrrole | — | 1.05 (9H), 4.10 (2H), 5.20 (1H), 6.90 (1H), 7.10 (2H), 7.30 (1H), 8.00 (1H) |
| 39 | 4-Cl-C₆H₄-OCH₂CH(CH(CH₃)₂)COCON-pyrrole | — | 1.05 (6H), 2.22 (1H), 4.10 (2H), 5.05 (1H), 6.6–7.2 (4H), 6.92 (1H), 7.30 (1H), 8.0 (1H) |
| 40 | 4-Cl-C₆H₄-OCH₂CH(n-C₄H₉)COCON-pyrrole | — | 0.80–1.90 (9H), 4.10 (2H), 5.10 (1H), 6.6–7.2 (4H), 6.90 (1H), 7.30 (1H), 8.0 (1H) |
| 41 | 4-Cl-C₆H₄-OCH₂CH(iso-C₄H₉)COCON-pyrrole | — | 0.80–1.90 (9H), 4.10 (2H), 5.30 (1H), 6.60–7.20 (4H), 6.90 (1H), 7.30 (1H), 8.00 (1H) |
| 42 | 4-Cl-C₆H₄-OCH₂CH(cyclohexyl)COCON-pyrrole | m.p. 37–38° C. | 0.9–1.1 (11H), 4.10 (2H), 5.10 (1H), 6.6–7.2 (4H), 6.90 (1H), 7.30 (1H), 8.0 (1H) |
| 43 | 4-(CH₃)₂CH-C₆H₄-OCH₂CH(CH(CH₃)₂)COCON-pyrrole | — | 1.1 (6H), 1.22 (6H), 2.2 (1H), 2.8 (1H), 4.10 (2H), 5.10 (1H), 6.6–7.2 (4H), 6.90 (1H), 7.30 (1H), 8.0 (1H) |
| 44 | 4-tert-C₄H₉-C₆H₄-OCH₂CH(CH(CH₃)₂)COCON-pyrrole | — | 1.05 (6H), 1.22 (9H), 2.2 (1H), 4.10 (2H), 5.10 (1H), 6.6–7.2 (4H), 6.90 (1H), 7.30 (1H), 8.00 (1H) |
| 45 | 4-CH₃O-C₆H₄-OCH₂CH(CH(CH₃)₂)COCON-pyrrole | — | 1.05 (6H), 2.2 (1H), 3.62 (3H), 4.05 (2H), 5.05 (1H), 6.68 (4H), 6.90 (1H), 7.28 (1H), 7.98 (1H) |
| 46 | C₆H₅-OCH₂CH(CH₃)COCON-pyrrole | — | 1.45 (3H), 4.40 (2H), 5.28 (1H), 6.60–7.30 (7H), 7.90 (1H) |
| 47 | CH₃CH₂OOC-C₆H₄-OCH₂CH(C(CH₃)₃)-OC(O)N-pyrrole | m.p. 85.8° C. | 1.08 (9H), 1.33 (3H), 4.15 (2H), 4.22 (2H), 5.15 (1H), 6.70 (2H), 6.90 (1H), 7.25 (1H), 7.78 (2H), 7.97 (1H) |

TABLE 1-continued

| Ex. No. | Formula | Property | NMR spectrum (CDCl₃) δ ppm |
|---|---|---|---|
| 48 | CH₃(CH₂)₂OOC—⟨C₆H₄⟩—OCH₂CH(C(CH₃)₃)—OC(=O)—N(imidazole) | m.p. 85.0° C. | 0.98 (3H), 1.08 (9H), 1.65 (2H), 4.10 (2H), 4.15 (2H), 5.13 (1H), 6.68 (2H), 6.90 (1H), 7.25 (1H), 7.80 (2H), 7.98 (1H) |
| 49 | CH₂=CHCH₂OOC—⟨C₆H₄⟩—OCH₂CH(C(CH₃)₃)—OC(=O)—N(imidazole) | m.p. 81.4° C. | 1.09 (9H), 4.15 (2H), 4.65 (2H), 5.00–5.40 (3H), 5.85 (1H), 6.70 (2H), 6.90 (1H), 7.25 (1H), 7.80 (2H), 7.98 (1H) |
| 50 | CH₃OOC—⟨C₆H₄⟩—OCH₂CH(C(CH₃)₃)—OC(=O)—N(imidazole) | oil | 1.09 (9H), 3.72 (3H), 4.15 (2H), 5.13 (1H), 6.70–7.55 (6H), 7.93 (1H) |
| 51 | CH₃(CH₂)₃OOC—⟨C₆H₄⟩—OCH₂CH(C(CH₃)₃)—OC(=O)—N(imidazole) | oil | 0.93 (3H), 1.08 (9H), 1.20–1.70 (4H), 4.15 (2H), 4.20 (2H), 5.15 (1H), 6.70–7.60 (6H), 7.96 (1H) |
| 52 | C₆H₅CH₂OOC—⟨C₆H₄⟩—OCH₂CH(C(CH₃)₃)—OC(=O)—N(imidazole) | oil | 1.09 (9H), 4.15 (2H), 5.17 (1H), 5.25 (2H), 6.80–7.60 (11H), 8.00 (1H) |
| 53 | CH₃—NHC(=O)—⟨C₆H₄⟩—OCH₂CH(C(CH₃)₃)—OC(=O)—N(imidazole) | m.p. 147.3° C. | 1.08 (9H), 2.95 (3H), 4.15 (2H), 5.12 (1H), 6.40 (1H), 6.67 (2H), 6.90 (1H), 7.27 (1H), 7.55 (2H), 7.95 (1H) |
| 54 | CH₃(CH₂)₂—NHC(=O)—⟨C₆H₄⟩—OCH₂CH(C(CH₃)₃)—OC(=O)—N(imidazole) | m.p. 134.9° C. | 0.93 (3H), 1.08 (9H), 1.57 (2H), 3.26 (2H), 4.15 (2H), 5.12 (1H), 6.28 (1H), 6.68 (2H), 6.90 (1H), 7.26 (1H), 7.55 (2H), 7.95 (1H) |
| 55 | C₆H₅—NHC(=O)—⟨C₆H₄⟩—OCH₂CH(C(CH₃)₃)—OC(=O)—N(imidazole) | m.p. 118.1° C. | 1.05 (9H), 4.15 (2H), 5.15 (1H), 6.68 (2H), 6.90 (1H), 6.90–7.55 (6H), 7.65 (1H), 7.95 (1H), 8.40 (1H) |
| 56 | C₂H₅—NHC(=O)—O—⟨C₆H₄⟩—OCH₂CH(C(CH₃)₃)—OC(=O)—N(imidazole) | oil | 1.06 (9H), 1.18 (3H), 3.35 (2H), 4.13 (2H), 5.13 (1H), 6.55 (1H), 6.70–7.30 (6H), 7.92 (1H) |
| 57 | (CH₃)₂CH—NHC(=O)—O—⟨C₆H₄⟩—OCH₂CH(C(CH₃)₃)—OC(=O)—N(imidazole) | m.p. 54.8° C. | 1.07 (9H), 1.15 (6H), 4.13 (3H), 5.10 (1H), 6.48 (1H), 6.70–7.30 (6H), 7.90 (1H) |
| 58 | (CH₃)₂NC(=O)—O—⟨C₆H₄⟩—OCH₂CH(C(CH₃)₃)—OC(=O)—N(imidazole) | oil | 1.09 (9H), 2.95 (6H), 4.15 (2H), 5.15 (1H), 6.60–7.35 (6H), 8.00 (1H) |

TABLE 1-continued

| Ex. No. | Formula | Property | NMR spectrum (CDCl₃) δ ppm |
|---|---|---|---|
| 59 | 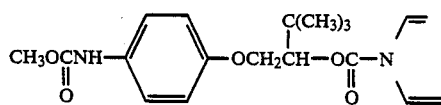 | m.p. 83–85° C. | 1.04 (9H), 3.62 (3H), 4.10 (2H), 5.16 (1H), 6.56–7.40 (7H), 7.98 (1H) |
| 60 | 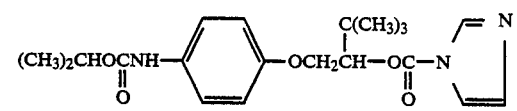 | yellow oil | 1.06 (9H), 1.26 (6H), 4.12 (2H), 4.88 (1H), 5.12 (1H), 6.58–7.40 (7H), 7.98 (1H) |
| 61 | 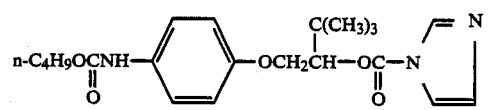 | yellow oil | 0.70–1.90 (7H), 1.08 (9H), 4.08 (2H), 4.12 (2H), 5.16 (1H), 6.58–7.40 (7H), 7.90 (1H) |
| 62 | 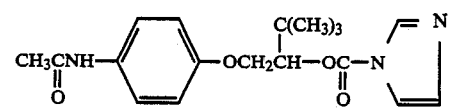 | yellow oil | 1.08 (9H), 2.06 (3H), 4.16 (2H), 5.12 (1H), 6.58–7.40 (6H), 7.60 (1H), 8.0 (1H) |
| 63 | 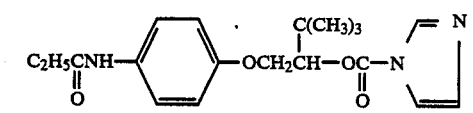 | yellow oil | 1.08 (9H), 1.12 (3H), 2.22 (2H), 4.12 (2H), 5.12 (1H), 6.58–7.42 (6H), 8.0 (1H), 8.60 (1H) |
| 64 | 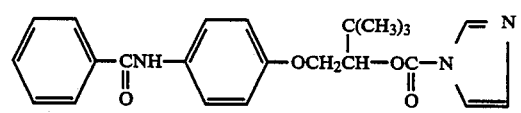 | m.p. 40–42° C. | 1.08 (9H), 4.16 (2H), 5.16 (1H), 6.60–7.80 (11H), 7.98 (1H), 8.74 (1H), |
| 65 | 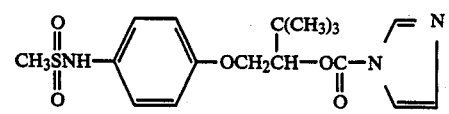 | yellow oil | 1.10 (9H), 2.84 (3H), 4.18 (2H), 5.18 (1H), 6.64–7.40 (6H), 8.02 (1H), 8.30 (1H), |
| 66 | 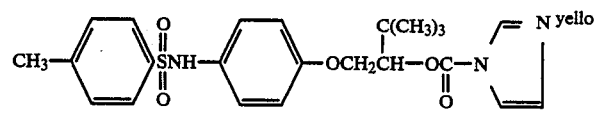 | yellow oil | 1.06 (9H), 2.30 (3H), 4.16 (2H), 5.12 (1H), 6.70–7.42 (10H), 7.80 (1H), 8.90 (1H) |
| 67 | 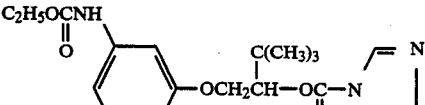 | yellow oil | 1.08 (9H), 1.26 (3H), 3.90–4.30 (4H), 5.16 (1H), 6.30–7.40 (7H), 8.0 (1H) |
| 68 | 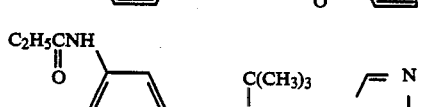 | yellow oil | 1.04 (9H), 1.18 (3H), 2.30 (2H), 4.12 (2H), 5.12 (1H), 6.30–7.40 (6H), 7.98 (1H), 8.60 (1H) |
| 69 | 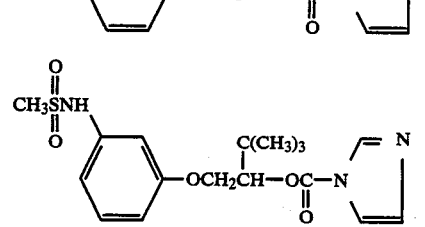 | yellow oil | 1.08 (9H), 2.84 (3H), 4.18 (2H), 5.16 (1H), 6.30–7.42 (6H), 7.90 (1H), 8.42 (1H) |

EXAMPLE 70

Preparation of 1'-(p-chlorophenyl)-3',3'-dimethyl-2'-butyl imidazol-1-yl-carboxylate A 2.14 g quantity of 1-(p-chlorophenyl)-3,3-dimethyl-2-butanol and 0.78 g of pyridine were placed into 30 ml of ethyl acetate and cooled to a temperature of up to 10° C. A 0.6 ml quantity of trichloromethyl chloroformate was added dropwise in small portions to the mixture with stirring. The resulting mixture was stirred at room temperature for 1 hour. with addition of 0.68 g of imidazole and 0.78 g of pyridine, the mixture was subsequently heated to 70° to 80° C. for 2 hours. The reaction mixture was cooled to room temperature, washed with water, dried over anhydrous sodium sulfate and distilled to evaporate off the solvent, giving 2.9 g of the above-identified desired compound.

M.p.: 121.5°–122° C.

| Elementary analysis: | C | H | N |
|---|---|---|---|
| Calcd. for $C_{16}H_{19}N_2ClO_2$ (%) | 62.72 | 6.26 | 9.15 |
| Found (%) | 62.60 | 6.23 | 9.22 |

NMR spectrum (CDCl$_3$) δ ppm: 1.06 (s, 9H), 2.9 (m, 2H), 5.0 (m, 1H), 6.9 (m, 1H), 6.9–7.1 (m, 4H), 7.2 (m, 1H), 7.9 (m, 1H).

These results indicated that the compound obtained was

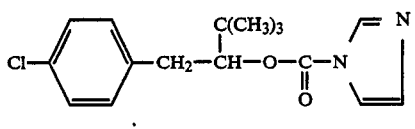

EXAMPLE 71

Preparation of 1′-(p-chlorophenyl)-2′-cyclohexylethyl imidazol-1-yl-carboxylate

A 2.40 g quantity of 1-(p-chlorophenyl)-2-cyclohexyl ethanol and 2.0 g of N,N′-carbonyldiimidazole were placed into 30 ml of ethyl acetate, and the mixture was refluxed for 3 hours with stirring. The reaction mixture was then cooled to room temperature, washed with water twice and thereafter dried over anhydrous magnesium sulfate. The product was distilled to remove the solvent, giving 3.3 g of the above-identified desired compound.

M.p.: 80.5°–81° C.

| Elementary analysis: | C | H | N |
|---|---|---|---|
| Calcd. for $C_{18}H_{21}N_2ClO_2$ (%) | 65.03 | 6.37 | 8.43 |
| Found (%) | 65.21 | 6.32 | 8.50 |

NMR spectrum (CDCl$_3$) δ ppm: 0.7–2.0 (m, 11H), 2.9 (m, 2H), 5.0 (m, 1H), 6.9 (m, 1H), 6.7–7.2 (m, 4H), 7.2 (m, 1H), 7.9 (m, 1H).

These results indicated that the compound obtained was

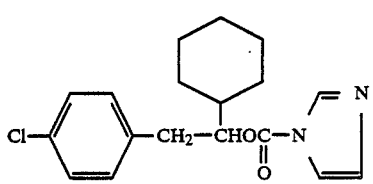

EXAMPLES 72–100

The compounds listed in Table 2 below were prepared in the same manner as in Example 70 or 71 using suitable starting materials.

TABLE 2

| Ex. No. | Formula | Property | NMR spectrum (CDCl$_3$) δ ppm |
|---|---|---|---|
| 72 | phenyl-CH$_2$-CH(C(CH$_3$)$_3$)-O-C(=O)-N(imidazolyl) | m.p. 98.5–99° C. | 1.06 (s, 9H), 2.9 (m, 2H), 5.0 (m, 1H), 6.7–7.2 (m, 7H), 7.9 (m, 1H) |
| 73 | Cl-phenyl-CH$_2$-CH(CH(CH$_3$)$_2$)-O-C(=O)-N(imidazolyl) | m.p. 70–70.5° C. | 0.9–1.2 (m, 6H), 2.0 (m, 1H), 2.9 (m, 2H), 5.0 (m, 1H), 6.9 (m, 1H), 6.9–7.1 (m, 4H), 7.2 (m, 1H), 7.9 (m, 1H) |
| 74 | Cl-phenyl-CH$_2$-CH(CH(CH$_3$)(C$_2$H$_5$))-O-C(=O)-N(imidazolyl) | m.p. 72.5–73° C. | 0.7–2.0 (m, 9H), 2.9 (m, 2H), 5.1 (m, 1H), 6.9 (m, 1H), 7.0–7.1 (m, 4H), 7.2 (m, 1H), 6.9 (m, 1H) |
| 75 | Br-phenyl-CH$_2$-CH(C(CH$_3$)$_3$)-O-C(=O)-N(imidazolyl) | m.p. 128–128.5° C. | 1.06 (s, 9H), 2.9 (m, 2H), 5.0 (m, 1H), 6.9 (m, 1H), 6.7–7.1 (m, 4H), 7.2 (m, 1H), 7.9 (m, 1H) |
| 76 | F-phenyl-CH$_2$-CH(C(CH$_3$)$_3$)-O-C(=O)-N(imidazolyl) | m.p. 109.5–110° C. | 1.06 (s, 9H), 2.9 (m, 2H), 5.0 (m, 1H), 6.9 (m, 1H), 6.9–7.1 (m, 4H), 7.2 (m, 1H), 7.9 (m, 7H) |
| 77 | CH$_3$-phenyl-CH$_2$-CH(C(CH$_3$)$_3$)-O-C(=O)-N(imidazolyl) | m.p. 90–90.5° C. | 1.06 (s, 9H), 2.2 (s, 3H), 2.9 (m, 2H), 5.0 (m, 1H), 6.9–7.1 (m, 4H), 7.2 (m, 1H), 6.9 (m, 1H) |

TABLE 2-continued
| Ex. No. | Formula | Property | NMR spectrum (CDCl$_3$) δ ppm |
|---|---|---|---|
| 78 | 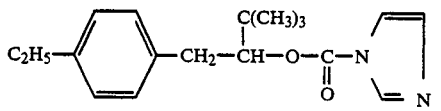 | m.p. 82–82.5° C. | 1.1 (s, 9H), 1.3 (m, 3H), 2.2 (m, 2H), 2.9 (m, 2H), 5.0 (m, 1H), 6.9 (m, 1H9, 6.9–7.1 (m, 4H), 7.2 (m, 1H) 7.9 (m, 1H) |
| 79 | 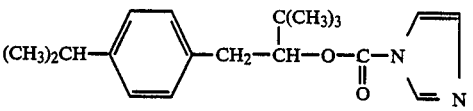 | m.p. 86.5–87° C. | 1.1 (s, 9H), 1.3 (d, 6H), 2.1 (m, 1H), 3.0 (m, 2H), 5.0 (m, 1H), 6.9 (m, 1H), 6.9–7.1 (m, 4H) 7.2 (m, 1H), 7.9 (m, 7H) |
| 80 | 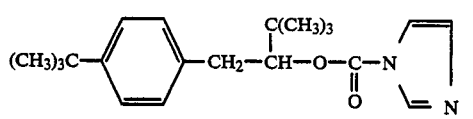 | m.p. 98–98.5° C. | 1.06 (s, 9H), 1.2 (s, 9H), 2.9 (m, 2H), 5.0 (m, 1H), 6.9 (m, 1H), 6.9–7.1 (m, 4H), 7.2 (m, 1H), 6.9 (m, 1H) |
| 81 | 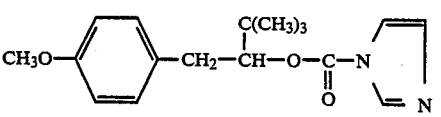 | m.p. 82.5–83° C. | 1.06 (s, 9H), 2.9 (m, 2H), 3.7 (s, 3H), 5.0 (m, 1H), 6.9 (m, 1H), 7.0–7.2 (m, 4H), 7.2 (m, 1H), 7.9 (m, 1H) |
| 82 | 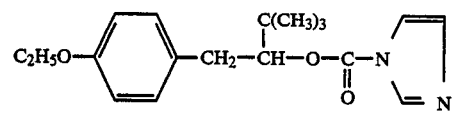 | m.p. 81.5–82° C. | 1.1 (s, 9H), 1.3 (m, 3H), 2.9 (m, 2H), 4.0 (m, 2H), 5.0 (m, 1H), 6.9 (m, 1H), 6.9–7.1 (m, 4H), 7.2 (m, 1H), 7.9 (m, 1H) |
| 83 | 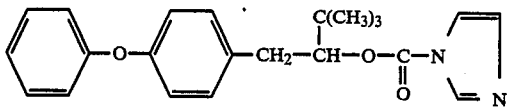 | m.p. 80.5–81° C. | 1.06 (s, 9H), 3.0 (m, 2H), 5.0 (m, 1H), 6.7–7.3 (m, 11H), 7.9 (m, 1H) |
| 84 | 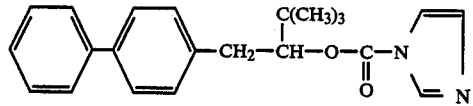 | m.p. 111.5–112° C. | 1.06 (s, 9H), 3.0 (m, 2H), 5.0 (m, 1H), 6.7–7.4 (m, 11H), 7.9 (m, 1H) |
| 85 | 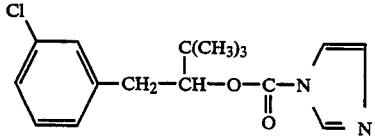 | m.p. 97–97.5° C. | 1.06 (s, 9H), 3.0 (m, 2H), 5.1 (m, 1H), 6.8–7.2 (m, 6H), 7.9 (m, 1H) |
| 86 | 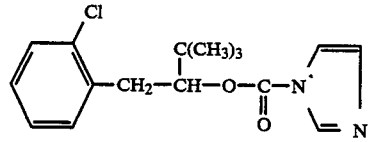 | m.p. 113.5–114° C. | 1.06 (s, 9H), 3.0 (m, 2H), 5.1 (m, 1H), 6.8–7.3 (m, 6H), 7.9 (m, 1H) |
| 87 | 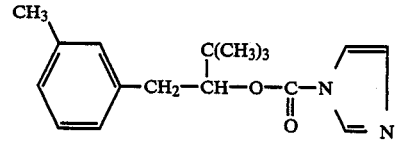 | m.p. 93–93.5° C. | 1.06 (s, 9H), 2.2 (s, 3H), 2.9 (m, 2H), 5.0 (m, 1H), 6.8–7.2 (m, 6H), 7.9 (m, 1H) |
| 88 | 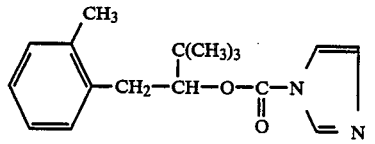 | m.p. 97–97.5° C. | 1.1 (s, 9H), 2.3 (s, 3H), 3.0 (m, 2H), 5.0 (m, 1H), 6.7–7.2 (m, 6H), 7.9 (m, 1H) |
| 89 | 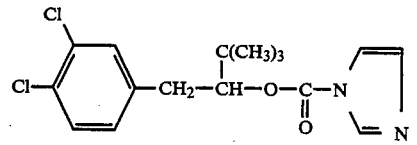 | m.p. 106.5–107° C. | 1.06 (s, 9H), 2.9 (m, 2H), 5.0 (m, 1H), 6.9 (m, 1H), 7.05–7.2 (m, 3H), 7.22 (m, 1H), 7.9 (m, 1H) |

TABLE 2-continued

| Ex. No. | Formula | Property | NMR spectrum (CDCl₃) δ ppm |
|---|---|---|---|
| 90 | 2,4-dichlorobenzyl derivative with C(CH₃)₃, CH₂-CH-O-C(=O)-N(imidazole) | m.p. 90.5-91° C. | 1.1 (s, 9H), 3.0 (m, 2H), 5.0 (m, 1H), 6.8-7.2 (m, 5H), 7.9 (m, 1H) |
| 91 | 3,5-dichlorobenzyl derivative with C(CH₃)₃, CH₂-CH-O-C(=O)-N(imidazole) | m.p. 99-99.5° C. | 1.1 (s, 9H), 3.0 (m, 2H), 5.0 (m, 1H), 6.8-7.2 (m, 5H), 7.9 (m, 1H) |
| 92 | CCl₂=CH-C₆H₄-CH₂-CH(C(CH₃)₃)-O-C(=O)-N(imidazole) | m.p. 112-112.5° C. | 1.1 (s, 9H), 3.0 (m, 2H), 5.0 (m, 1H), 6.8 (s, 1H), 6.8-7.2 (m, 6H), 7.9 (m, 1H) |
| 93 | 4-Cl-C₆H₄-CH₂-CH(CH(C₂H₅)₂)-O-C(=O)-N(imidazole) | m.p. 70.5-71° C. | 0.7-2.0 (m, 11H), 2.9 (m, 2H), 5.1 (m, 1H), 6.9 (m, 1H), 6.9-7.1 (m, 4H), 7.2 (m, 1H), 7.9 (m, 1H) |
| 94 | (CH₃)₃C-C₆H₄-CH₂-CH(CH₃)-O-C(=O)-N(imidazole) | yellow oil | 1.1 (s, 9H), 1.3 (m, 3H), 2.9 (m, 2H), 5.0 (m, 1H), 6.9 (m, 1H), 6.9-7.1 (m, 4H), 7.2 (m, 1H), 7.9 (m, 1H) |
| 95 | 4-Cl-C₆H₄-CH₂-CH(n-C₃H₇CHCH₃)-O-C(=O)-N(imidazole) | m.p. 71.5-72° C. | 0.7-1.7 (m, 11H), 2.9 (m, 2H), 5.2 (m, 1H), 6.9 (m, 1H), 6.9-7.1 (m, 4H), 7.2 (m, 1H), 7.9 (m, 1H) |
| 96 | (CH₃)₃C-C₆H₄-CH₂-CH(C₂H₅)-O-C(=O)-N(imidazole) | yellow oil | 1.2 (m, 9H), 1.3 (m, 3H), 2.0 (m, 2H), 2.9 (m, 2H), 5.0 (m, 1H), 6.9 (m, 1H), 6.9-7.1 (m, 4H), 7.2 (m, 1H), 7.9 (m, 1H) |
| 97 | 4-Cl-C₆H₄-CH₂-CH((CH₃)₂CHCH₂)-O-C(=O)-N(imidazole) | m.p. 71.5-72° C. | 0.8-2.0 (m, 9H), 2.95 (m, 2H), 5.2 (m, 1H), 6.9 (m, 1H), 7.0-7.2 (m, 4H), 7.22 (m, 1H), 7.96 (m, 1H) |
| 98 | 4-CH₃-C₆H₄-CH₂-CH(C₂H₅CHCH₃)-O-C(=O)-N(imidazole) | m.p. 68-68.5° C. | 0.7-2.0 (m, 9H), 2.2 (s, 3H), 3.0 (m, 2H), 5.0 (m, 1H), 6.9 (m, 1H), 6.9-7.2 (m, 4H), 7.22 (m, 1H), 7.9 (m, 1H) |
| 99 | 4-Cl-C₆H₄-CH₂-CH(CH₃CH₂CH₂)-O-C(=O)-N(imidazole) | pale yellow oil | 0.8-2.3 (m, 7H), 2.9 (m, 2H), 5.2 (m, 1H), 6.9 (m, 1H), 6.9-7.2 (m, 4H), 7.2 (m, 1H), 7.9 (m, 1H) |
| 100 | (CH₃)₃C-C₆H₄-CH₂-CH((CH₃)₂CH)-O-C(=O)-N(imidazole) | white crystal m.p. 69.5-70° C. | 0.8-1.1 (m, 6H), 1.16 (s, 9H), 2.0 (m, 1H), 2.82 (m, 2H), 5.0 (m, 1H), 6.8 (m, 1H), 6.9-7.1 (m, 4H), 7.12 (m, 1H), 7.84 (m, 1H) |

EXAMPLE 101

Preparation of 1'-(p-chlorophenoxy)-3',3'-dimethyl-4'-chloro-2'-butyl imidazol-1-yl-carboxylate A 2.6 g quantity of 1-(p-chlorophenoxy)-3,3-dimethyl-4-chloro-2-butanol, 1.8 g of N,N'-carbonyldiimidazole and 40 ml of ethyl acetate were placed into a 100-ml egg plant type flask and refluxed for 3 hours. The reaction mixture was concentrated in a vacuum, and the resulting residue was purified by silica gel column chromatography, giving 2.1 g of the above-identified desired compound.

M.p.: 65.7° C.

| Elementary analysis: | C | H | N |
|---|---|---|---|
| Calcd. for $C_{16}H_{18}N_2O_3Cl_2$ (%) | 53.80 | 5.08 | 7.84 |
| Found (%) | 53.62 | 5.14 | 7.76 |

NMR spectrum (CDCl$_3$) δ ppm: 1.20 (6H), 3.45 (2H), 4.15 (2H), 5.40 (1H), 6.65 (2H), 6.90 (1H), 7.05 (2H), 7.30 (1H), 8.00 (1H).

These results indicated that the compound obtained was

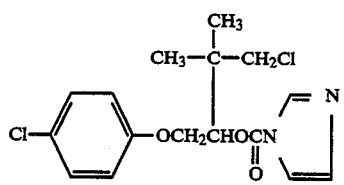

EXAMPLE 102

Preparation of 1'-(p-ethylphenoxy)-3',3'-dimethyl-4'-bromo-2'-butyl imidazol-1-yl-carboxylate A 3.0 g quantity of 1-(p-ethylphenoxy)-3,3-dimethyl-4-bromo-2-butanol, 0.81 ml of pyridine and 50 ml of ethyl acetate were placed into a 100-ml four-necked flask, and 0.6 ml of trichloromethyl chloroformate was added dropwise to the mixture with cooling and stirring. The mixture was thereafter stirred at room temperature for 18 hours and then cooled again. To the mixture were added 0.7 g of imidazole and 0.81 ml of pyridine, and the resulting mixture was stirred at room temperature for 30 minutes and further refluxed for 3 hours. The reaction mixture was washed with water and saturated aqueous solution of sodium chloride, dried over anhydrous magnesium sulfate and concentrated in a vacuum. The residue obtained was purified by silica gel column chromatography, giving 3.0 g of the above-identified desired compound.

M.p.: 47.1° C.

| Elementary analysis: | C | H | N |
|---|---|---|---|
| Calcd. for $C_{18}H_{23}N_2O_3Br$ (%) | 54.69 | 5.86 | 7.09 |
| Found (%) | 54.58 | 5.92 | 7.01 |

NMR spectrum (CDCl$_3$) δ ppm: 1.15 (3H), 1.20 (6H), 2.53 (2H), 3.35 (2H), 4.12 (2H), 5.40 (1H), 6.65 (2H), 6.90 (3H), 7.30 (1H), 8.00 (1H).

These results indicated that the compound obtained was

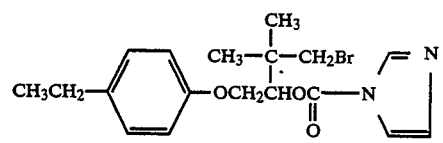

EXAMPLES 103-111

The compounds listed in Table 3 below were prepared in the same manner as in Example 101 or 102 using suitable starting materials.

TABLE 3

| Ex. No. | Formula | Property | NMR spectrum (CDCl$_3$) δ ppm |
|---|---|---|---|
| 103 | (structure with CH$_3$-C(CH$_3$)-CH$_2$Br, Cl-phenyl-OCH$_2$CHOC(O)-N-imidazole) | m.p. 67.6° C. | 1.02 (6H), 3.32 (2H), 4.10 (2H), 5.32 (1H), 6.58 (2H), 6.90 (1H), 7.03 (2H), 7.20 (1H), 7.93 (1H) |
| 104 | (structure with CH$_3$-C(CH$_3$)-CH$_2$OC(O)-CH$_3$, Cl-phenyl-OCH$_2$CHOC(O)-N-imidazole) | oil | 1.12 (6H), 2.00 (3H), 3.90 (2H), 4.10 (2H), 5.30 (1H), 6.62 (2H), 6.90 (1H), 7.05 (2H), 7.25 (1H) 7.95 (1H) |
| 105 | (structure with CH$_3$-C(CH$_3$)-CH$_2$OC(O)-phenyl, Cl-phenyl-OCH$_2$CHOC(O)-N-imidazole) | m.p. 85.4° C. | 1.20 (6H), 4.20 (4H), 5.45 (1H), 6.62 (2H), 6.90 (1H), 7.05 (2H), 7.10-7.50 (6H), 7.80 (1H), 7.95 (1H) |

TABLE 3-continued

| Ex. No. | Formula | Property | NMR spectrum (CDCl$_3$) δ ppm |
|---|---|---|---|
| 106 | (4-Cl-C$_6$H$_4$)-OCH$_2$CHOC(O)-N(imidazolyl), with CH(C(CH$_3$)$_2$COOC$_2$H$_5$) substituent | m.p. 51.3° C. | 1.20 (3H), 1.30 (6H), 4.05 (2H), 4.10 (2H), 5.55 (1H), 6.62 (2H), 6.90 (1H), 7.05 (2H), 7.12 (1H) 7.92 (1H) |
| 107 | (4-CH$_3$CH$_2$-C$_6$H$_4$)-OCH$_2$CHOC(O)-N(imidazolyl), with CH(C(CH$_3$)$_2$CH$_2$Cl) substituent | m.p. 64.5° C. | 1.15 (3H), 1.20 (6H), 2.55 (2H), 3.45 (2H), 4.20 (2H), 5.40 (1H), 6.68 (2H), 6.90 (1H), 6.95 (2H) 7.30 (1H), 8.00 (1H) |
| 108 | (4-CH$_3$CH$_2$-C$_6$H$_4$)-OCH$_2$CHOC(O)-N(imidazolyl), with CH(C(CH$_3$)$_2$CH$_2$OCCH$_3$(O)) substituent | oil | 1.12 (6H), 1.15 (3H), 2.00 (3H), 2.53 (2H), 3.90 (2H), 4.15 (2H), 5.35 (1H), 6.63 (2H), 6.90 (1H), 6.95 (2H), 7.28 (1H), 7.98 (1H) |
| 109 | (4-CH$_3$CH$_2$-C$_6$H$_4$)-OCH$_2$CHOC(O)-N(imidazolyl), with CH(C(CH$_3$)$_2$CH$_2$OC(O)C$_6$H$_5$) substituent | oil | 1.15 (3H), 1.20 (6H), 2.52 (2H), 4.20 (2H), 5.42 (1H), 6.60 (1H), 6.85 (1H), 6.90 (2H), 7.25 (4H) 7.65 (1H), 7.92 (1H) |
| 110 | (4-CH$_3$CH$_2$-C$_6$H$_4$)-OCH$_2$CHOC(O)-N(imidazolyl), with CH(C(CH$_3$)$_2$COOC$_2$H$_5$) substituent | oil | 1.15 (3H), 1.18 (3H), 1.30 (6H), 2.45 (2H), 4.00 (2H), 4.07 (2H), 5.50 (1H), 6.58 (2H), 6.83 (1H) 6.90 (2H), 7.20 (1H), 7.90 (1H) |
| 111 | (C$_6$H$_5$)-OCH$_2$CHOC(O)-N(imidazolyl), with CH(C(CH$_3$)$_2$COOC$_2$H$_5$) substituent | oil | 1.20 (3H), 1.30 (6H), 4.02 (2H), 4.10 (2H), 5.52 (1H), 6.55–7.25 (7H), 7.90 (1H), |

EXAMPLE 112

Preparation of
1′-(p-chlorophenoxy)-3,′,3′-dimethyl-2′-butyl imidazol-1-yl-thiocarboxylate A 2.3 g quantity of 1-(p-chlorophenoxy)-3,3-dimethyl-2-butanol, 0.81 ml of pyridine and 50 ml of ethyl acetate were placed into a 100-ml four-necked flask, and 0.77 ml of thiophosgene was added dropwise to the mixture with cooling in an ice bath and stirring. The mixture was thereafter stirred at room temperature for 18 hours. To the mixture were then added 0.7 g of imidazole and 0.81 ml of pyridine, and the resulting mixture was refluxed for 3 hours. The reaction mixture was washed with water and saturated aqueous solution of sodium chloride, dried over anhydrous magnesium sulfate and concentrated in a vacuum. The residue obtained was purified by silica gel column chromatography, giving 1.5 g of the above-identified desired compound in an oily form.

| Elementary analysis: | C | H | N |
|---|---|---|---|
| Calcd. for C$_{16}$H$_{19}$N$_2$O$_2$SCl (%) | 56.71 | 5.65 | 8.27 |
| Found (%) | 56.43 | 5.88 | 8.10 |

NMR spectrum (CDCl$_3$) δ ppm: 1.10 (9H), 4.14 (2H), 5.72 (1H), 6.60 (2H), 6.88 (1H), 7.04 (2H), 7.45 (1H), 8.18 (1H).

These results indicated that the compound obtained was

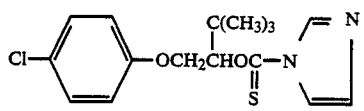

EXAMPLE 113

Preparation of
1'-(p-ethylphenoxy)-3',3'-dimethyl-2'-butyl
imidazol-1-yl-thiocarboxylate A 2.2 g quantity of 1-(p-ethylphenoxy)-3,3-dimethyl-2-butanol, 0.81 ml of pyridine and 50 ml of ethyl acetate were placed into a 100-ml four-necked flask, and 0.77 ml of thiophosgene was added dropwise to the mixture with cooling in an ice bath and stirring. The mixture was thereafter stirred at room temperature for 18 hours. To the mixture were added 0.7 g of imidazole and 0.81 ml of pyridine, and the resulting mixture was refluxed for 3 hours. The reaction mixture was washed with water and saturated aqueous solution of sodium chloride, dried over anhydrous magnesium sulfate and concentrated in a vacuum. The residue obtained was purified by silica gel column chromatography, giving 1.3 g of the above-identified desired compound in the form of an oil.

| Elementary analysis: | C | H | N |
|---|---|---|---|
| Calcd. for $C_{18}H_{24}N_2O_2S$ (%) | 65.03 | 7.28 | 8.43 |
| Found (%) | 64.97 | 7.34 | 8.31 |

NMR spectrum ($CDCl_3$) δ ppm: 1.10 (9H), 1.16 (3H), 2.52 (2H), 4.18 (2H), 5.72 (1H), 6.60 (2H), 6.85 (1H), 6.92 (1H), 7.45 (1H), 8.15 (1H).

These results indicated that the compound obtained was

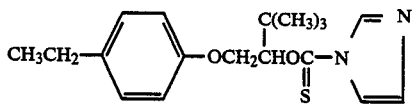

EXAMPLE 114

Preparation of
1'-(p-chlorophenyl)-4',4'-dimethyl-3'-amyl
imidazol-1-yl-thiocarboxylate A 2.3 g quantity of 1-(p-chlorophenyl)-4,4-dimethyl-3-amyl alcohol, 0.81 ml of pyridine and 50 ml of ethyl acetate were placed into a 100-ml four-necked flask, and 0.77 ml of thiophosgene was added dropwise to the mixture with cooling and stirring. The mixture was thereafter stirred at room temperature for 18 hours and then cooled again. To the mixture were added 0.7 g of imidazole and 0.81 ml of pyridine, and the resulting mixture was stirred at room temperature for 30 minutes and further refluxed for 3 hours. The reaction mixture was washed with water and saturated aqueous solution of sodium chloride, dried over anhydrous magnesium sulfate and concentrated in a vacuum. The residue obtained was purified by silica gel column chromatography, giving 1.1 g of the above-identified desired compound.

M.p.: 66.5° C.

| Elementary analysis: | C | H | N |
|---|---|---|---|
| Calcd. for $C_{17}H_{21}N_2OSCl$ (%) | 60.61 | 6.28 | 8.32 |
| Found (%) | 60.42 | 6.35 | 8.28 |

NMR spectrum ($CDCl_3$) δ ppm: 0.98 (9H), 2.05 (2H), 2.62 (2H), 5.55 (1H), 6.92 (1H), 7.00 (4H), 7.48 (1H), 8.20 (1H).

These results indicated that the compound obtained was

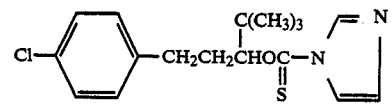

EXAMPLE 115

Preparation of
1'-(p-chlorophenyl)-3',3'-dimethyl-2'-butyl
imidazol-1-yl-thiocarboxylate A 2.1 g quantity of 1-(p-chlorophenyl)-3,3-dimethyl-2-butanol, 0.81 ml of pyridine and 50 ml of ethyl acetate were placed into a 100-ml four-necked flask, and 0.77 ml of thiophosgene was added dropwise to the mixture with cooling and stirring. The mixture was thereafter stirred at room temperature for 18 hours and then cooled again. To the mixture were added 0.7 g of imidazole and 0.81 ml of pyridine, and the resulting mixture was stirred at room temperature for 30 minutes and further refluxed for 3 hours. The reaction mixture was washed with water and saturated aqueous solution of sodium chloride, dried over anhydrous magnesium sulfate and concentrated in a vacuum. The residue obtained was purified by silica gel column chromatography, giving 1.2 g of the above-identified desired compound.

M.p.: 86.8° C.

| Elementary analysis: | C | H | N |
|---|---|---|---|
| Calcd. for $C_{16}H_{19}N_2OSCl$ (%) | 59.52 | 5.93 | 8.68 |
| Found (%) | 59.31 | 6.01 | 8.73 |

NMR spectrum ($CDCl_3$) δ ppm: 1.10 (9H), 2.92 (2H), 5.65 (1H), 6.88 (1H), 7.00 (4H), 7.40 (1H), 8.12 (1H).

These results indicated that the compound obtained was

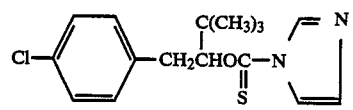

EXAMPLES 116–132

The compounds listed in Table 4 below were prepared in the same manner as in Examples 112, 113, 114 and 115 using suitable starting materials.

TABLE 4

| Ex. No. | Formula | Property | NMR spectrum (CDCl$_3$) δ ppm |
|---|---|---|---|
| 116 | Ph-OCH$_2$CH(C(CH$_3$)$_3$)OC(=S)-N(CH=N-CH=CH) | oil | 1.10 (9H), 4.12 (2H), 5.78 (1H), 6.60–7.30 (6H), 7.50 (1H), 8.20 (1H) |
| 117 | 3-Cl-C$_6$H$_4$-OCH$_2$CH(C(CH$_3$)$_3$)OC(=S)-N(CH=N-CH=CH) | m.p. 41.2° C. | 1.10 (9H), 4.20 (2H), 5.72 (1H), 6.50–7.10 (5H), 7.47 (1H), 8.19 (1H) |
| 118 | 4-Br-C$_6$H$_4$-OCH$_2$CH(C(CH$_3$)$_3$)OC(=S)-N(CH=N-CH=CH) | oil | 1.10 (9H), 4.17 (2H), 5.72 (1H), 6.75 (2H), 6.86 (1H), 7.18 (2H), 7.45 (1H), 8.17 (1H) |
| 119 | 4-CH$_3$-C$_6$H$_4$-OCH$_2$CH(C(CH$_3$)$_3$)OC(=S)-N(CH=N-CH=CH) | oil | 1.10 (9H), 2.20 (3H), 4.16 (2H), 5.75 (1H), 6.56 (2H), 6.83 (1H), 6.90 (2H), 7.45 (1H), 8.15 (1H) |
| 120 | 3-CH$_3$-C$_6$H$_4$-OCH$_2$CH(C(CH$_3$)$_3$)OC(=S)-N(CH=N-CH=CH) | oil | 1.10 (9H), 2.20 (3H), 4.16 (2H), 5.73 (1H), 6.40–6.70 (3H), 6.88 (1H), 6.90 (1H), 7.45 (1H), 8.15 (1H) |
| 121 | CH$_3$(CH$_2$)$_2$-C$_6$H$_4$-OCH$_2$CH(C(CH$_3$)$_3$)OC(=S)-N(CH=N-CH=CH) | oil | 0.88 (3H), 1.10 (9H), 1.52 (2H), 2.45 (2H), 4.15 (2H), 5.72 (1H), 6.57 (2H), 6.83 (1H), 6.90 (2H), 7.46 (1H), 8.15 (1H) |
| 122 | (CH$_3$)$_2$CH-C$_6$H$_4$-OCH$_2$CH(C(CH$_3$)$_3$)OC(=S)-N(CH=N-CH=CH) | oil | 1.10 (9H), 2.75 (1H), 4.18 (2H), 5.75 (1H), 6.65 (2H), 6.85 (1H), 6.93 (2H), 7.45 (1H), 8.15 (1H) |
| 123 | (CH$_3$)$_3$C-C$_6$H$_4$-OCH$_2$CH(C(CH$_3$)$_3$)OC(=S)-N(CH=N-CH=CH) | oil | 1.10 (9H), 1.26 (9H), 4.16 (2H), 5.75 (1H), 6.60 (2H), 6.85 (1H), 7.10 (1H), 7.42 (1H), 8.13 (1H) |
| 124 | biphenyl-OCH$_2$CH(C(CH$_3$)$_3$)OC(=S)-N(CH=N-CH=CH) | oil | 1.10 (9H), 4.20 (2H), 5.75 (1H), 6.73 (2H), 6.85 (1H), 7.05–7.45 (8H), 8.20 (2H) |
| 125 | CH$_3$O-C$_6$H$_4$-OCH$_2$CH(C(CH$_3$)$_3$)OC(=S)-N(CH=N-CH=CH) | oil | 1.10 (9H), 3.65 (3H), 4.15 (2H), 5.70 (1H), 6.60 (4H), 6.86 (1H), 7.45 (1H), 8.15 (1H) |

TABLE 4-continued

| Ex. No. | Formula | Property | NMR spectrum (CDCl₃) δ ppm |
|---|---|---|---|
| 126 | [3,4-dichlorophenyl-OCH₂CH(C(CH₃)₃)OC(=S)-N(imidazol-1-yl)] | m.p. 94.1° C. | 1.10 (9H), 4.15 (2H), 5.70 (1H), 6.60 (1H), 6.85 (1H), 6.92 (1H), 7.15 (1H), 7.45 (1H), 8.15 (1H) |
| 127 | [3,4-dimethylphenyl-OCH₂CH(C(CH₃)₃)OC(=S)-N(imidazol-1-yl)] | m.p. 59.0° C. | 1.10 (9H), 2.12 (6H), 4.15 (2H), 5.70 (1H), 6.40 (2H), 6.75 (1H), 6.82 (1H), 7.40 (1H), 8.10 (1H) |
| 128 | [phenyl-CH₂CH₂CH(C(CH₃)₃)OC(=S)-N(imidazol-1-yl)] | oil | 1.00 (9H), 2.08 (2H), 2.60 (2H), 5.55 (1H), 6.90 (4H), 7.05 (5H), 7.45 (1H), 8.15 (1H) |
| 129 | [4-isopropylphenyl-OCH₂CH₂CH(C(CH₃)₃)OC(=S)-N(imidazol-1-yl)] | oil | 0.98 (9H), 1.05 (6H), 2.00 (2H), 2.60 (2H), 5.55 (1H), 6.88 (1H), 6.92 (4H), 7.45 (1H), 8.15 (1H) |
| 130 | [4-methoxyphenyl-CH₂CH₂CH(C(CH₃)₃)OC(=S)-N(imidazol-1-yl)] | oil | 0.98 (9H), 2.00 (2H), 2.60 (2H), 3.62 (3H), 5.53 (1H), 6.60 (2H), 6.88 (1H), 6.92 (2H), 7.45 (1H), 8.15 (1H) |
| 131 | [3,4-dichlorophenyl-CH₂CH₂CH(C(CH₃)₃)OC(=S)-N(imidazol-1-yl)] | m.p. 101.3° C. | 0.98 (9H), 2.05 (2H), 2.60 (2H), 5.55 (1H), 6.80 (1H), 6.90 (1H), 7.10 (2H), 7.45 (1H), 8.15 (1H) |
| 132 | [phenyl-CH₂CH(C(CH₃)₃)OC(=S)-N(imidazol-1-yl)] | oil | 1.08 (9H), 2.96 (2H), 5.65 (1H), 6.82 (1H), 7.00 (5H), 7.40 (1H), 8.10 (1H) |

EXAMPLE 133

Preparation of 1'-(p-chlorophenylthio)-3',3'-dimethyl-2'-butyl imidazol-1-yl-carboxylate A 2.4 g quantity of 1-(p-chlorophenylthio)-3,3-dimethyl-2-butanol and 2.0 g of N,N'-carbonyldiimidazole were placed into 30 ml of ethyl acetate, and the mixture was refluxed for 3 hours with stirring. The reaction mixture was then cooled to room temperature, washed with water twice, dried over anhydrous magnesium sulfate and distilled to remove the solvent. The residue was purified by silica gel column chromatography, giving 2.9 g of the above-identified desired compound in the form of a pale yellow oil.

| Elementary analysis: | C | H | N |
|---|---|---|---|
| Calcd. for C₁₆H₁₉N₂SO₂Cl (%) | 56.71 | 5.65 | 8.27 |
| Found (%) | 56.89 | 5.64 | 8.30 |

NMR spectrum (CDCl₃) δ ppm: 0.92 (9H), 3.62 (2H), 4.92 (1H), 6.62–7.30 (6H), 7.90 (1H).

These results indicated that the compound obtained was

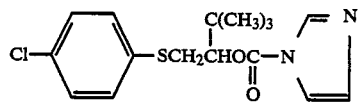

EXAMPLE 134

Preparation of 1'-(o-chlorophenylthio)-3',3'-dimethyl-2'-butyl imidazol-1-yl-carboxylate A 2.4 g quantity of 1-(o-chlorophenylthio)-3,3-dimethyl-2-butanol and 0.8 g of pyridine were dissolved in 30 ml of ethyl acetate, and 0.6 ml of trichloromethyl chloroformate was added dropwise in small portions to the solution while the solution was being cooled at a temperature of up to 10° C. With addition of 0.8 g of pyridine and 0.7 g of imidazole, the mixture was then refluxed for 3 hours with stirring. The mixture resulting from the reaction was washed with water, dried and concentrated. The residue was purified by silica gel column chromatography, giving 2.8 g of the above-identified desired compound in the form of a pale yellow oil.

| Elementary analysis: | C | H | N |
|---|---|---|---|
| Calcd. for $C_{16}H_{19}N_2SO_2Cl$ (%) | 56.71 | 5.65 | 8.27 |
| Found (%) | 56.82 | 5.63 | 8.29 |

NMR spectrum (CDCl$_3$) δ ppm: 0.91 (9H), 3.65 (2H), 5.01 (1H), 6.5–7.3 (6H), 7.90 (1H).

These results indicated that the compound obtained was

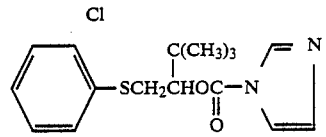

EXAMPLE 135–149

The compounds listed in Table 5 below were prepared in the same manner as in Example 133 or 134 using suitable staring materials.

TABLE 5

| Ex. No. | Formula | Property | NMR spectrum (CDCl$_3$) δ ppm |
|---|---|---|---|
| 135 | (phenyl)-SCH$_2$CHOC(=O)-N(imidazole), C(CH$_3$)$_3$ | yellow oil | 0.92 (9H), 3.04 (2H), 4.90 (1H), 6.8 (1H), 7.0–7.40 (6H), 7.90 (1H) |
| 136 | Br-(phenyl)-SCH$_2$CHOC(=O)-N(imidazole), C(CH$_3$)$_3$ | yellow oil | 0.92 (9H), 3.02 (2H), 4.92 (1H), 6.68–7.32 (6H), 7.88 (1H) |
| 137 | CH$_3$-(phenyl)-SCH$_2$CHOC(=O)-N(imidazole), C(CH$_3$)$_3$ | yellow oil | 0.92 (9H), 2.30 (3H), 3.02 (2H), 4.90 (1H), 6.68–7.32 (6H), 7.90 (1H) |
| 138 | (CH$_3$)$_3$C-(phenyl)-SCH$_2$CHOC(=O)-N(imidazole), C(CH$_3$)$_3$ | yellow oil | 0.94 (9H), 1.02 (9H), 3.02 (2H), 4.92 (1H), 6.60–7.32 (6H), 7.90 (1H) |
| 139 | C$_2$H$_5$-(phenyl)-SCH$_2$CHOC(=O)-N(imidazole), C(CH$_3$)$_3$ | yellow oil | 0.92 (9H), 1.30 (3H), 2.40 (2H), 3.02 (2H), 4.92 (1H), 6.72–7.30 (6H), 7.88 (1H) |
| 140 | (CH$_3$)$_2$CH-(phenyl)-SCH$_2$CHOC(=O)-N(imidazole), C(CH$_3$)$_3$ | yellow oil | 0.92 (9H), 1.02–1.30 (6H), 2.42 (1H), 3.02 (2H), 4.90 (1H), 6.68–7.32 (6H), 7.90 (1H) |
| 141 | CH$_3$O-(phenyl)-SCH$_2$CHOC(=O)-N(imidazole), C(CH$_3$)$_3$ | yellow oil | 0.94 (9H), 3.02 (2H), 3.70 (3H), 4.92 (1H), 6.60–7.36 (3H), 7.92 (1H) |
| 142 | C$_2$H$_5$O-(phenyl)-SCH$_2$CHOC(=O)-N(imidazole), C(CH$_3$)$_3$ | yellow oil | 0.92 (9H), 1.32 (3H), 3.0 (2H), 3.88 (2H), 4.88 (1H), 6.54–7.30 (6H), 7.88 (1H) |
| 143 | Cl,Cl-(phenyl)-SCH$_2$CHOC(=O)-N(imidazole), C(CH$_3$)$_3$ | yellow oil | 0.92 (9H), 3.02 (2H), 4.92 (1H), 6.62–7.30 (5H), 7.90 (1H) |
| 144 | CH≡CCH$_2$O-(phenyl)-SCH$_2$CHOC(=O)-N(imidazole), C(CH$_3$)$_3$ | yellow oil | 0.92 (9H), 2.50 (1H), 3.04 (2H), 4.52 (2H), 6.62–7.32 (6H), 7.88 (1H) |

TABLE 5-continued

| Ex. No. | Formula | Property | NMR spectrum (CDCl₃) δ ppm |
|---|---|---|---|
| 145 | CH₂=CCH₂O—⟨⟩—SCH₂CHOC—N(imidazole), with C(CH₃)₃ branch and CH₃ on vinyl | yellow oil | 0.92 (9H), 1.80 (3H), 3.02 (2H), 4.30 (1H), 4.92 (2H), 6.60–7.36 (6H), 7.90 (1H) |
| 146 | 3-Cl-4-CH₃-phenyl—SCH₂CHOC—N(imidazole), C(CH₃)₃ branch | yellow oil | 0.92 (9H), 2.32 (3H), 3.08 (2H), 4.92 (1H), 6.70–7.32 (5H), 7.88 (1H) |
| 147 | 3-CH₃-phenyl—SCH₂CHOC—N(imidazole), C(CH₃)₃ branch | yellow oil | 0.92 (9H), 2.30 (3H), 3.02 (2H), 4.90 (1H) 6.70–7.32 (6H), 7.90 (1H) |
| 148 | 2-CH₃-phenyl—SCH₂CHOC—N(imidazole), C(CH₃)₃ branch | yellow oil | 0.92 (9H), 2.32 (3H), 3.04 (2H), 4.90 (1H), 6.68–7.32 (6H), 7.90 (1H) |
| 149 | 2,4,5-trichlorophenyl—SCH₂CHOC—N(imidazole), C(CH₃)₃ branch | yellow oil | 0.92 (9H), 3.02 (2H), 4.92 (1H), 6.8–7.32 (4H), 7.90 (1H) |

EXAMPLE 150

Preparation of 1'-(p-chlorophenoxy)-2'-methyl-2'-propyl imidazol-1-yl-carboxylate A 2.0 g quantity of 1-(p-chlorophenoxy)-2-methyl-2-propanol and 2.0 g of N,N'-carbonyldiimidazole were placed into 30 ml of ethyl acetate, and the mixture was refluxed for 3 hours with stirring. The reaction mixture was then cooled to room temperature, washed with water twice, dried over anhydrous magnesium sulfate and distilled to remove the solvent. The residue was purified by silica gel column chromatography, giving 2.4 g of the above-identified desired compound in the form of a pale yellow oil.

| Elementary analysis: | C | H | N |
|---|---|---|---|
| Calcd. for C₁₄H₁₅N₂O₃Cl (%) | 59.056 | 5.310 | 9.838 |
| Found (%) | 59.224 | 5.278 | 9.921 |

NMR spectrum (CDCl₃) δ ppm: 1.62 (6H), 4.10 (2H), 6.60–7.22 (6H), 7.88 (1H).

These results indicated that the compound obtained was

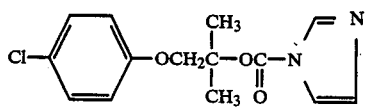

EXAMPLE 151

Preparation of 1'-(p-chlorophenoxy)-2',3'-dimethyl-2'-butyl imidazol-1-yl-carboxylate A 2.9 g quantity of 1-(p-chlorophenoxy)-2,3-dimethyl-2-butanol and 0.8 g of pyridine were placed into 30 ml of ethyl acetate, and the mixture was stirred at a temperature of up to 10° C. A 0.6 ml quantity of trichloromethyl chloroformate was added dropwise in small portions to the mixture. The resulting mixture was thereafter stirred at room temperature for 2 hours. Subsequently, 0.8 g of pyridine and 0.7 g of imidazole were added to the mixture, and the mixture was refluxed with stirring for 3 hours, thereafter cooled to room temperature, washed with water, dried over anhydrous magnesium sulfate and distilled to remove the solvent. The residue was purified by silica gel column chromatography, giving 2.8 g of the above-identified desired compound in the form of a pale yellow oil.

| Elementary analysis: | C | H | N |
|---|---|---|---|
| Calcd. for C₁₆H₁₉N₂O₃Cl (%) | 59.536 | 5.933 | 8.678 |
| Found (%) | 59.712 | 5.892 | 8.704 |

NMR spectrum (CDCl₃) δ ppm: 1.20 (6H), 1.62 (3H), 2.40 (1H), 4.18 (2H), 6.6–7.30 (6H), 7.90 (1H).

These results indicated that the compound obtained was

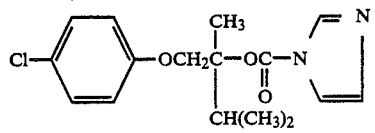

EXAMPLES 152-178

The compounds listed in Table 6 below were prepared in the same manner as in Example 150 or 151 using suitable starting materials.

TABLE 6

| Ex. No. | Formula | Property | NMR spectrum (CDCl₃) δ ppm |
|---|---|---|---|
| 152 | (phenyl)-OCH₂C(CH₃)(CH₃)-OC(=O)-N(pyrrole) | yellow oil | 1.68 (6H), 4.10 (2H), 6.7-7.3 (7H), 7.90 (1H) |
| 153 | Cl-(C₆H₄)-OCH₂C(CH₃)(CH(CH₃)(C₂H₅))-OC(=O)-N(pyrrole) | yellow oil | 0.88-2.34 (8H), 1.60 (3H), 4.12 (2H), 6.62-7.20 (6H), 7.88 (1H) |
| 154 | Cl-(C₆H₄)-OCH₂C(CH₃)(cyclohexyl)-OC(=O)-N(pyrrole) | yellow oil | 0.9-2.40 (11H), 1.60 (3H), 4.10 (2H), 6.62-7.24 (6H), 7.88 (1H) |
| 155 | Cl-(C₆H₄)-OCH₂C(C₂H₅)(CH(CH₃)₂)-OC(=O)-N(pyrrole) | yellow oil | 0.9-2.72 (12H), 4.18 (1H), 6.60-7.22 (7H), 7.90 (1H) |
| 156 | Cl-(C₆H₄)-OCH₂C(n-C₃H₇)(n-C₃H₇)-OC(=O)-N(pyrrole) | yellow oil | 0.8-2.3 (14H), 4.12 (2H), 6.60-7.22 (6H), 7.88 (1H) |
| 157 | Cl-(C₆H₄)-OCH₂C(cyclohexyl)(cyclohexyl)-OC(=O)-N(pyrrole) | yellow oil | 0.9-2.42 (22H), 4.18 (2H), 6.6-7.30 (6H), 7.88 (1H) |
| 158 | Cl₂C=CH-(C₆H₄)-OCH₂C(C₂H₅)(CH(CH₃)₂)-OC(=O)-N(pyrrole) | yellow oil | 1.68 (6H), 4.10 (2H), 6.6-7.4 (7H), 7.88 (1H) |
| 159 | Cl₂C=CH-(C₆H₄)-OCH₂C(CH₃)(CH(CH₃)₂)-OC(=O)-N(pyrrole) | yellow oil | 1.2 (6H), 1.62 (3H), 2.40 (1H), 4.18 (2H), 6.6-7.30 (7H), 7.90 (1H) |

TABLE 6-continued
| Ex. No. | Formula | Property | NMR spectrum (CDCl$_3$) δ ppm |
|---|---|---|---|
| 160 | 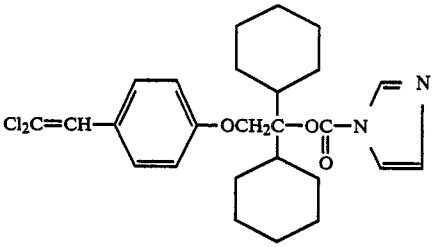 | yellow oil | 0.9–2.42 (22H), 4.12 (2H), 6.6–7.30 (7H), 7.90 (1H) |
| 161 | 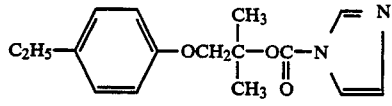 | yellow oil | 1.2 (3H), 1.68 (6H), 2.50 (2H), 4.08 (2H), 6.6–7.2 (6H), 7.88 (1H) |
| 162 | 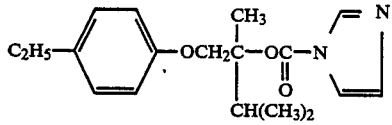 | yellow oil | 0.9–1.8 (9H), 1.55 (3H), 2.3–2.8 (3H), 4.22 (2H), 6.60–7.20 (6H), 7.88 (1H) |
| 163 | 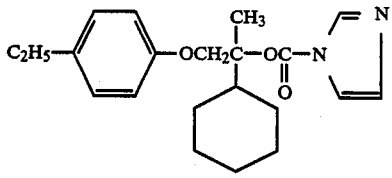 | yellow oil | 1.1 (3H), 0.9–2.0 (11H), 1.6 (3H), 2.40 (2H), 4.20 (2H), 6.6–7.2 (6H), 7.88 (1H) |
| 164 | 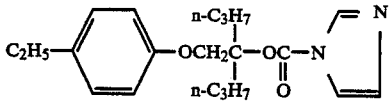 | yellow oil | 0.82–2.60 (19H), 4.14 (2H), 6.60–7.22 (6H), 7.88 (1H) |
| 165 | 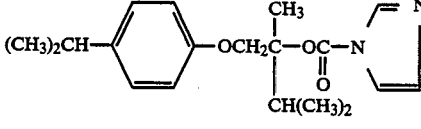 | yellow oil | 0.9–1.34 (12H), 1.60 (3H), 2.4–3.0 (2H), 4.30 (2H), 6.60–7.22 (6H), 7.90 (1H) |
| 166 | 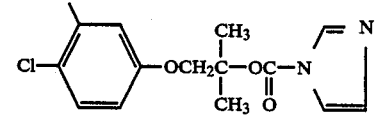 | yellow oil | 1.60 (6H), 4.10 (2H), 6.70–7.26 (5H), 7.90 (1H) |
| 167 | 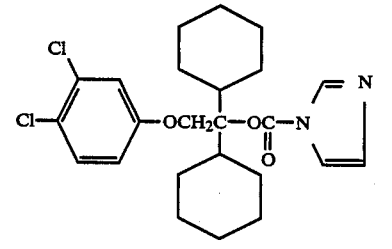 | yellow oil | 0.90–2.42 (22H), 4.12 (2H), 0.62–7.30 (5H), 7.88 (1H) |
| 168 | 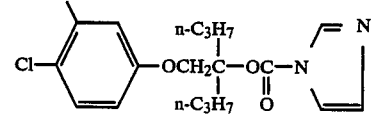 | yellow oil | 0.82–2.40 (14H), 4.10 (2H), 0.62–7.30 (5H), 7.88 (1H) |

TABLE 6-continued

| Ex. No. | Formula | Property | NMR spectrum (CDCl₃) δ ppm |
|---|---|---|---|
| 169 | (CH₃)₂CH—C₆H₄—OCH₂C(CH₃)(C₆H₁₁)—OC(O)—N(pyrazole) | yellow oil | 1.2 (6H), 0.9–2.3 (11H), 1.60 (3H), 4.24 (2H), 6.6–7.2 (6H), 7.90 (1H) |
| 170 | C₂H₅O—C₆H₄—OCH₂C(CH₃)₂—OC(O)—N(pyrazole) | yellow oil | 1.36 (3H), 1.70 (6H), 3.88 (2H), 4.08 (2H), 6.70 (4H), 6.88 (1H), 7.18 (1H), 7.90 (1H) |
| 171 | C₂H₅O—C₆H₄—OCH₂C(CH₃)(CH(CH₃)₂)—OC(O)—N(pyrazole) | yellow oil | 0.9–1.8 (9H), 1.60 (3H), 2.40 (1H), 3.88 (2H), 4.18 (2H), 6.70 (4H), 6.88 (1H), 7.18 (1H), 7.90 (1H) |
| 172 | C₂H₅O—C₆H₄—OCH₂C(n-C₃H₇)₂—OC(O)—N(pyrazole) | yellow oil | 0.8–2.3 (17H), 3.88 (2H), 4.18 (2H), 6.68 (4H), 6.90 (1H), 7.20 (1H), 7.90 (1H) |
| 173 | C₂H₅O—C₆H₄—OCH₂C(CH₃)(C₆H₁₁)—OC(O)—N(pyrazole) | yellow oil | 1.3 (3H), 0.9–2.4 (11H), 1.60 (3H), 3.82 (2H), 4.22 (2H), 6.68 (4H), 6.90 (1H), 7.20 (1H), 6.90 (1H) |
| 174 | (CH₃)₃C—C₆H₄—OCH₂C(CH₃)₂—OC(O)—N(pyrazole) | yellow oil | 1.30 (9H), 1.70 (3H), 4.10 (2H), 6.68–7.30 (6H), 7.90 (1H) |
| 175 | CH₃O—C₆H₄—OCH₂C(CH₃)₂—OC(O)—N(pyrazole) | yellow oil | 1.68 (6H), 3.70 (3H), 4.10 (2H), 6.70 (4H), 6.88 (1H), 7.18 (1H), 7.90 (1H) |
| 176 | (CH₃)₂CH—C₆H₄—OCH₂C(CH₃)₂—OC(O)—N(pyrazole) | yellow oil | 1.22 (3H), 1.70 (6H), 2.8 (1H), 4.1 (2H), 6.65–7.22 (6H), 7.90 (1H) |
| 177 | Br—C₆H₄—OCH₂C(CH₃)₂—OC(O)—N(pyrazole) | yellow oil | 1.62 (6H), 4.12 (2H), 6.60–7.22 (6H), 7.88 (1H) |
| 178 | CF₃—C₆H₄—OCH₂C(CH₃)₂—OC(O)—N(pyrazole) | yellow oil | 1.60 (6H), 4.10 (2H), 6.62–7.22 (6H), 7.88 (1H) |

FORMULATION EXAMPLE 1

(25% wettable powder)

| Ingredient | Parts by wt. |
|---|---|
| Compound of invention | 25 |
| White carbon | 45 |
| Kieselguhr | 16 |
| Sodium salt of higher alcohol sulfate | 2 |
| Sodium salt of β-naphthalenesulfonic acid-formalin condensation product | 2 |
| Alkyl phenyl phenol sulfate | 10 |
| | 100 |

The above ingredients were thoroughly mixed together by a mixer and finely divided by a pulverizer to obtain a 25% wettable powder.

FORMULATION EXAMPLE 2

(20% emulsificable concentrate)

| Ingredient | Parts by wt. |
|---|---|
| Compound of invention | 20 |
| Polyoxyethylene styryl phenyl ether | 8 |
| Sodium dodecylbenzenesulfonate | 4 |
| Xylene | 68 |
| | 100 |

The above ingredients were mixed together to obtain a 20% emulsificable concentrate.

TEST EXAMPLE 1

Control effect on cucumber powdery mildew

The wettable powder prepared in Formulation Example 1 was sprayed, as diluted to a specified concentration, onto cucumber seedlings (in two- to three-leaf stage) planted in 200-ml pots (7.5 cm in diameter). After the composition dried in air, a suspension of spores of *Sphaerotheca fuliginea* causing the above disease was sprayed onto the seedlings for inoculation. Two weeks thereafter, the lesion area percentage was determined, and the control effect was calculated from the following equation.

$$\% \text{ Diseases control} = \frac{\text{Untreated \% diseases} - \text{Treated \% diseases}}{\text{Untreated \% diseases}} \times 100$$

The seedlings were also checked for phytotoxicity. Table 7 shows the results.

TABLE 7

| Compound No. | Concentration (ppm) | Control effect (%) | Phytotoxicity |
|---|---|---|---|
| 1 | 12.5 | 92 | none |
| 2 | 12.5 | 90 | none |
| 3 | 12.5 | 95 | none |
| 4 | 12.5 | 100 | none |
| 5 | 12.5 | 100 | none |
| 6 | 12.5 | 95 | none |
| 10 | 12.5 | 100 | none |
| 11 | 12.5 | 100 | none |
| 12 | 12.5 | 93 | none |
| 13 | 12.5 | 100 | none |
| 14 | 12.5 | 100 | none |
| 17 | 12.5 | 95 | none |
| 18 | 12.5 | 92 | none |
| 19 | 12.5 | 90 | none |
| 22 | 12.5 | 97 | none |
| 26 | 12.5 | 95 | none |
| 32 | 12.5 | 100 | none |
| 39 | 12.5 | 95 | none |
| 43 | 12.5 | 92 | none |
| 44 | 12.5 | 90 | none |
| 45 | 12.5 | 90 | none |
| 47 | 12.5 | 95 | none |
| 48 | 12.5 | 90 | none |
| 49 | 12.5 | 92 | none |
| 50 | 12.5 | 66 | none |
| 51 | 12.5 | 70 | none |
| 52 | 12.5 | 60 | none |
| 53 | 12.5 | 80 | none |
| 54 | 12.5 | 85 | none |
| 55 | 12.5 | 60 | none |
| 56 | 12.5 | 65 | none |
| 58 | 12.5 | 60 | none |

TABLE 7-continued

| Compound No. | Concentration (ppm) | Control effect (%) | Phytotoxicity |
|---|---|---|---|
| 59 | 12.5 | 80 | none |
| 60 | 12.5 | 85 | none |
| 61 | 12.5 | 85 | none |
| 63 | 12.5 | 90 | none |
| 64 | 12.5 | 75 | none |
| 65 | 12.5 | 80 | none |
| 66 | 12.5 | 60 | none |
| 67 | 12.5 | 60 | none |
| 68 | 12.5 | 65 | none |
| 69 | 12.5 | 60 | none |
| 70 | 12.5 | 100 | none |
| 71 | 12.5 | 90 | none |
| 72 | 12.5 | 96 | none |
| 73 | 12.5 | 92 | none |
| 75 | 12.5 | 100 | none |
| 76 | 12.5 | 100 | none |
| 77 | 12.5 | 98 | none |
| 78 | 12.5 | 95 | none |
| 79 | 12.5 | 100 | none |
| 80 | 12.5 | 95 | none |
| 81 | 12.5 | 95 | none |
| 85 | 12.5 | 92 | none |
| 86 | 12.5 | 90 | none |
| 87 | 12.5 | 90 | none |
| 88 | 12.5 | 92 | none |
| 89 | 12.5 | 90 | none |
| 92 | 12.5 | 98 | none |
| 96 | 12.5 | 85 | none |
| 97 | 12.5 | 90 | none |
| 99 | 12.5 | 95 | none |
| 101 | 12.5 | 100 | none |
| 102 | 12.5 | 98 | none |
| 103 | 12.5 | 100 | none |
| 104 | 12.5 | 74 | none |
| 105 | 12.5 | 66 | none |
| 106 | 12.5 | 60 | none |
| 107 | 12.5 | 100 | none |
| 108 | 12.5 | 82 | none |
| 109 | 12.5 | 75 | none |
| 110 | 12.5 | 68 | none |
| 111 | 12.5 | 57 | none |
| 112 | 12.5 | 100 | none |
| 113 | 12.5 | 95 | none |
| 114 | 12.5 | 85 | none |
| 115 | 12.5 | 100 | none |
| 116 | 12.5 | 90 | none |
| 117 | 12.5 | 87 | none |
| 118 | 12.5 | 100 | none |
| 119 | 12.5 | 90 | none |
| 120 | 12.5 | 85 | none |
| 121 | 12.5 | 97 | none |
| 122 | 12.5 | 100 | none |
| 123 | 12.5 | 95 | none |
| 124 | 12.5 | 100 | none |
| 125 | 12.5 | 92 | none |
| 126 | 12.5 | 88 | none |
| 127 | 12.5 | 85 | none |
| 128 | 12.5 | 65 | none |
| 129 | 12.5 | 80 | none |
| 130 | 12.5 | 95 | none |
| 131 | 12.5 | 73 | none |
| 132 | 12.5 | 93 | none |
| 133 | 12.5 | 95 | none |
| 134 | 12.5 | 80 | none |
| 135 | 12.5 | 83 | none |
| 136 | 12.5 | 98 | none |
| 137 | 12.5 | 90 | none |
| 138 | 12.5 | 90 | none |
| 139 | 12.5 | 85 | none |
| 140 | 12.5 | 80 | none |
| 141 | 12.5 | 90 | none |
| 142 | 12.5 | 86 | none |
| 143 | 12.5 | 75 | none |
| 144 | 12.5 | 75 | none |
| 145 | 12.5 | 80 | none |
| 146 | 12.5 | 85 | none |
| 147 | 12.5 | 75 | none |
| 148 | 12.5 | 75 | none |
| 149 | 12.5 | 70 | none |
| 150 | 12.5 | 95 | none |

TABLE 7-continued

| Compound No. | Concentration (ppm) | Control effect (%) | Phytotoxicity |
|---|---|---|---|
| 151 | 12.5 | 90 | none |
| 152 | 12.5 | 80 | none |
| 153 | 12.5 | 90 | none |
| 154 | 12.5 | 60 | none |
| 155 | 12.5 | 75 | none |
| 156 | 12.5 | 68 | none |
| 157 | 12.5 | 63 | none |
| 158 | 12.5 | 90 | none |
| 159 | 12.5 | 86 | none |
| 161 | 12.5 | 92 | none |
| 162 | 12.5 | 90 | none |
| 163 | 12.5 | 72 | none |
| 164 | 12.5 | 69 | none |
| 166 | 12.5 | 83 | none |
| 168 | 12.5 | 72 | none |
| 170 | 12.5 | 90 | none |
| 171 | 12.5 | 86 | none |
| 174 | 12.5 | 89 | none |
| 176 | 12.5 | 90 | none |
| 177 | 12.5 | 93 | none |

TEST EXAMPLE 2

Control effect on cucumber gray mold

The wettable powder prepared in Formulation Example 1 was sprayed, as diluted to a specified concentration, onto cucumber seedlings (in two- to three-leaf stage) planted in 200-ml pots (7.5 cm in diameter). After the composition dried in air, a suspension of spores of *Botrytis cinerea* causing the above disease was sprayed onto the seedlings for inoculation. Seven days thereafter, the lesion area percentage was determined, and the control effect was calculated in the same manner as in Test Example 1. The seedlings were also checked for phytotoxicity.

Table 8 shows the results.

TABLE 8

| Compound No. | Concentration (ppm) | Control effect (%) | Phytotoxicity |
|---|---|---|---|
| 1 | 200 | 60 | none |
| 2 | 200 | 52 | none |
| 3 | 200 | 75 | none |
| 4 | 200 | 100 | none |
| 5 | 200 | 100 | none |
| 6 | 200 | 100 | none |
| 10 | 200 | 100 | none |
| 11 | 200 | 100 | none |
| 12 | 200 | 75 | none |
| 13 | 200 | 93 | none |
| 14 | 200 | 97 | none |
| 15 | 200 | 64 | none |
| 16 | 200 | 50 | none |
| 17 | 200 | 73 | none |
| 18 | 200 | 65 | none |
| 19 | 200 | 50 | none |
| 20 | 200 | 55 | none |
| 21 | 200 | 48 | none |
| 22 | 200 | 83 | none |
| 26 | 200 | 85 | none |
| 30 | 200 | 90 | none |
| 32 | 200 | 100 | none |
| 35 | 200 | 85 | none |
| 37 | 200 | 85 | none |
| 47 | 200 | 100 | none |
| 48 | 200 | 95 | none |
| 49 | 200 | 100 | none |
| 51 | 200 | 84 | none |
| 53 | 200 | 66 | none |
| 54 | 200 | 70 | none |
| 55 | 200 | 60 | none |
| 56 | 200 | 75 | none |
| 57 | 200 | 75 | none |
| 58 | 200 | 60 | none |
| 59 | 200 | 90 | none |
| 60 | 200 | 90 | none |
| 61 | 200 | 95 | none |
| 62 | 200 | 80 | none |
| 63 | 200 | 85 | none |
| 64 | 200 | 68 | none |
| 65 | 200 | 82 | none |
| 66 | 200 | 80 | none |
| 67 | 200 | 65 | none |
| 68 | 200 | 70 | none |
| 69 | 200 | 65 | none |
| 70 | 200 | 90 | none |
| 72 | 200 | 85 | none |
| 73 | 200 | 70 | none |
| 74 | 200 | 65 | none |
| 75 | 200 | 100 | none |
| 76 | 200 | 100 | none |
| 77 | 200 | 90 | none |
| 78 | 200 | 95 | none |
| 79 | 200 | 90 | none |
| 80 | 200 | 85 | none |
| 81 | 200 | 90 | none |
| 84 | 200 | 80 | none |
| 86 | 200 | 65 | none |
| 87 | 200 | 70 | none |
| 88 | 200 | 60 | none |
| 92 | 200 | 60 | none |
| 94 | 200 | 75 | none |
| 95 | 200 | 70 | none |
| 96 | 200 | 60 | none |
| 97 | 200 | 55 | none |
| 101 | 200 | 100 | none |
| 102 | 200 | 100 | none |
| 103 | 200 | 96 | none |
| 104 | 200 | 74 | none |
| 105 | 200 | 68 | none |
| 106 | 200 | 55 | none |
| 107 | 200 | 100 | none |
| 108 | 200 | 82 | none |
| 109 | 200 | 78 | none |
| 110 | 200 | 62 | none |
| 111 | 200 | 50 | none |
| 112 | 200 | 75 | none |
| 113 | 200 | 100 | none |
| 114 | 200 | 88 | none |
| 115 | 200 | 100 | none |
| 116 | 200 | 65 | none |
| 117 | 200 | 60 | none |
| 118 | 200 | 100 | none |
| 119 | 200 | 55 | none |
| 120 | 200 | 45 | none |
| 121 | 200 | 80 | none |
| 122 | 200 | 70 | none |
| 123 | 200 | 65 | none |
| 124 | 200 | 74 | none |
| 125 | 200 | 100 | none |
| 126 | 200 | 55 | none |
| 127 | 200 | 43 | none |
| 128 | 200 | 66 | none |
| 129 | 200 | 75 | none |
| 130 | 200 | 92 | none |
| 131 | 200 | 45 | none |
| 132 | 200 | 83 | none |
| 133 | 200 | 85 | none |
| 134 | 200 | 64 | none |
| 135 | 200 | 70 | none |
| 136 | 200 | 95 | none |
| 137 | 200 | 100 | none |
| 138 | 200 | 85 | none |
| 139 | 200 | 95 | none |
| 140 | 200 | 95 | none |
| 141 | 200 | 90 | none |
| 142 | 200 | 85 | none |
| 143 | 200 | 64 | none |
| 144 | 200 | 72 | none |
| 145 | 200 | 65 | none |
| 146 | 200 | 60 | none |
| 147 | 200 | 66 | none |
| 148 | 200 | 70 | none |
| 149 | 200 | 75 | none |

TABLE 8-continued

| Compound No. | Concentration (ppm) | Control effect (%) | Phytotoxicity |
|---|---|---|---|
| 150 | 200 | 83 | none |
| 151 | 200 | 78 | none |
| 152 | 200 | 70 | none |
| 153 | 200 | 70 | none |
| 154 | 200 | 65 | none |
| 155 | 200 | 76 | none |
| 156 | 200 | 66 | none |
| 157 | 200 | 60 | none |
| 158 | 200 | 90 | none |
| 161 | 200 | 88 | none |
| 162 | 200 | 75 | none |
| 163 | 200 | 62 | none |
| 165 | 200 | 80 | none |
| 167 | 200 | 60 | none |
| 169 | 200 | 65 | none |
| 172 | 200 | 70 | none |
| 174 | 200 | 85 | none |
| 175 | 200 | 90 | none |
| 176 | 200 | 88 | none |
| 177 | 200 | 90 | none |
| 178 | 200 | 90 | none |

TEST EXAMPLE 3

Curing effect on rice blast

A suspension of spores of *Pyricularia oryzae* causing the above disease was sprayed onto rice seedlings (in four-leaf stage) planted in 200-ml pots (7.5 cm in diameter). Twenty-four hours thereafter, the emulsifiable concentrate prepared in Formulation Example 2 was sprayed as diluted to a specified concentration onto the rice seedlings. Seven days thereafter, the lesion area percentage was determined, and the control effect was calculated in the same manner as in Test Example 1. The seedlings were also checked for phytotoxicity.

Table 9 shows the results.

TABLE 9

| Compound No. | Concentration (ppm) | Control effect (%) | Phytotoxicity |
|---|---|---|---|
| 1 | 500 | 90 | none |
| 2 | 500 | 65 | none |
| 3 | 500 | 95 | none |
| 4 | 500 | 93 | none |
| 5 | 500 | 100 | none |
| 6 | 500 | 77 | none |
| 10 | 500 | 100 | none |
| 11 | 500 | 85 | none |
| 12 | 500 | 88 | none |
| 13 | 500 | 70 | none |
| 14 | 500 | 75 | none |
| 17 | 500 | 83 | none |
| 18 | 500 | 64 | none |
| 22 | 500 | 95 | none |
| 26 | 500 | 98 | none |
| 29 | 500 | 100 | none |
| 30 | 500 | 98 | none |
| 31 | 500 | 96 | none |
| 32 | 500 | 100 | none |
| 34 | 500 | 98 | none |
| 43 | 500 | 72 | none |
| 47 | 500 | 80 | none |
| 48 | 500 | 85 | none |
| 49 | 500 | 90 | none |
| 50 | 500 | 62 | none |
| 51 | 500 | 60 | none |
| 52 | 500 | 55 | none |
| 53 | 500 | 77 | none |
| 54 | 500 | 80 | none |
| 55 | 500 | 64 | none |
| 56 | 500 | 60 | none |
| 57 | 500 | 62 | none |
| 58 | 500 | 60 | none |
| 59 | 500 | 82 | none |
| 60 | 500 | 85 | none |
| 63 | 500 | 60 | none |
| 64 | 500 | 60 | none |
| 65 | 500 | 65 | none |
| 66 | 500 | 60 | none |
| 67 | 500 | 66 | none |
| 68 | 500 | 68 | none |
| 69 | 500 | 70 | none |
| 70 | 500 | 100 | none |
| 71 | 500 | 60 | none |
| 72 | 500 | 90 | none |
| 73 | 500 | 75 | none |
| 74 | 500 | 60 | none |
| 75 | 500 | 100 | none |
| 76 | 500 | 100 | none |
| 77 | 500 | 95 | none |
| 78 | 500 | 90 | none |
| 79 | 500 | 95 | none |
| 80 | 500 | 85 | none |
| 81 | 500 | 90 | none |
| 89 | 500 | 75 | none |
| 90 | 500 | 65 | none |
| 91 | 500 | 60 | none |
| 92 | 500 | 90 | none |
| 97 | 500 | 75 | none |
| 98 | 500 | 80 | none |
| 99 | 500 | 85 | none |
| 100 | 500 | 60 | none |
| 101 | 500 | 100 | none |
| 102 | 500 | 96 | none |
| 103 | 500 | 100 | none |
| 104 | 500 | 82 | none |
| 105 | 500 | 71 | none |
| 106 | 500 | 46 | none |
| 107 | 500 | 100 | none |
| 108 | 500 | 76 | none |
| 109 | 500 | 58 | none |
| 110 | 500 | 53 | none |
| 111 | 500 | 44 | none |
| 112 | 500 | 100 | none |
| 113 | 500 | 80 | none |
| 114 | 500 | 95 | none |
| 115 | 500 | 100 | none |
| 116 | 500 | 64 | none |
| 117 | 500 | 55 | none |
| 118 | 500 | 100 | none |
| 119 | 500 | 75 | none |
| 120 | 500 | 68 | none |
| 121 | 500 | 78 | none |
| 122 | 500 | 90 | none |
| 123 | 500 | 88 | none |
| 124 | 500 | 85 | none |
| 125 | 500 | 100 | none |
| 126 | 500 | 95 | none |
| 127 | 500 | 80 | none |
| 128 | 500 | 88 | none |
| 129 | 500 | 95 | none |
| 130 | 500 | 73 | none |
| 131 | 500 | 100 | none |
| 132 | 500 | 81 | none |
| 133 | 500 | 100 | none |
| 134 | 500 | 80 | none |
| 135 | 500 | 85 | none |
| 136 | 500 | 100 | none |
| 137 | 500 | 92 | none |
| 138 | 500 | 75 | none |
| 139 | 500 | 90 | none |
| 140 | 500 | 95 | none |
| 141 | 500 | 90 | none |
| 142 | 500 | 85 | none |
| 143 | 500 | 68 | none |
| 144 | 500 | 74 | none |
| 145 | 500 | 83 | none |
| 146 | 500 | 66 | none |
| 147 | 500 | 85 | none |
| 148 | 500 | 70 | none |
| 149 | 500 | 83 | none |
| 150 | 500 | 100 | none |
| 151 | 500 | 95 | none |
| 152 | 500 | 78 | none |
| 153 | 500 | 80 | none |

TABLE 9-continued

| Compound No. | Concentration (ppm) | Control effect (%) | Phytotoxicity |
| --- | --- | --- | --- |
| 154 | 500 | 70 | none |
| 157 | 500 | 70 | none |
| 158 | 500 | 96 | none |
| 159 | 500 | 90 | none |
| 164 | 500 | 90 | none |
| 165 | 500 | 85 | none |
| 166 | 500 | 73 | none |
| 167 | 500 | 65 | none |
| 168 | 500 | 70 | none |
| 170 | 500 | 90 | none |
| 171 | 500 | 85 | none |
| 172 | 500 | 80 | none |
| 173 | 500 | 72 | none |
| 174 | 500 | 90 | none |
| 176 | 500 | 94 | none |
| 177 | 500 | 96 | none |
| 178 | 500 | 90 | none |

TEST EXAMPLE 4

Control effect on helminthosporium leaf spots on rice

The emulsifiable concentrate prepared in Formulation Example 2 was sprayed, as diluted to a specified concentration, onto rice seedlings (in five-leaf stage) planted in 200-ml pots (7.5 cm in diameter). After the emulsion dried in air, a suspension of spores of *Cochliobolus miyabeanus* causing the above disease was sprayed onto the seedlings for inoculation. Seven days thereafter, the lesion area percentage was determined, and the control effect was calculated in the same manner as in Test Example 1. The seedlings were also checked for phytotoxicity.

Table 10 shows the results.

TABLE 10

| Compound No. | Concentration (ppm) | Control effect (%) | Phytotoxicity |
| --- | --- | --- | --- |
| 1 | 100 | 93 | none |
| 2 | 100 | 78 | none |
| 3 | 100 | 95 | none |
| 4 | 100 | 100 | none |
| 5 | 100 | 100 | none |
| 6 | 100 | 95 | none |
| 10 | 100 | 100 | none |
| 11 | 100 | 100 | none |
| 12 | 100 | 88 | none |
| 13 | 100 | 98 | none |
| 14 | 100 | 98 | none |
| 16 | 100 | 73 | none |
| 17 | 100 | 92 | none |
| 18 | 100 | 85 | none |
| 19 | 100 | 86 | none |
| 20 | 100 | 90 | none |
| 21 | 100 | 84 | none |
| 22 | 100 | 100 | none |
| 26 | 100 | 100 | none |
| 32 | 100 | 100 | none |
| 43 | 100 | 71 | none |
| 47 | 100 | 100 | none |
| 48 | 100 | 95 | none |
| 49 | 100 | 100 | none |
| 50 | 100 | 63 | none |
| 51 | 100 | 65 | none |
| 52 | 100 | 60 | none |
| 53 | 100 | 85 | none |
| 54 | 100 | 90 | none |
| 55 | 100 | 73 | none |
| 56 | 100 | 68 | none |
| 57 | 100 | 66 | none |
| 58 | 100 | 70 | none |
| 59 | 100 | 84 | none |
| 60 | 100 | 90 | none |
| 61 | 100 | 82 | none |
| 62 | 100 | 80 | none |
| 63 | 100 | 77 | none |
| 64 | 100 | 60 | none |
| 65 | 100 | 80 | none |
| 66 | 100 | 85 | none |
| 67 | 100 | 60 | none |
| 70 | 100 | 95 | none |
| 72 | 100 | 90 | none |
| 73 | 100 | 60 | none |
| 75 | 100 | 100 | none |
| 76 | 100 | 98 | none |
| 77 | 100 | 90 | none |
| 78 | 100 | 90 | none |
| 79 | 100 | 96 | none |
| 80 | 100 | 80 | none |
| 81 | 100 | 85 | none |
| 83 | 100 | 90 | none |
| 84 | 100 | 85 | none |
| 92 | 100 | 90 | none |
| 93 | 100 | 60 | none |
| 94 | 100 | 60 | none |
| 95 | 100 | 75 | none |
| 96 | 100 | 60 | none |
| 97 | 100 | 80 | none |
| 98 | 100 | 75 | none |
| 99 | 100 | 90 | none |
| 101 | 100 | 100 | none |
| 102 | 100 | 98 | none |
| 103 | 100 | 96 | none |
| 104 | 100 | 78 | none |
| 105 | 100 | 63 | none |
| 106 | 100 | 59 | none |
| 107 | 100 | 100 | none |
| 108 | 100 | 82 | none |
| 109 | 100 | 73 | none |
| 110 | 100 | 53 | none |
| 111 | 100 | 56 | none |
| 112 | 100 | 100 | none |
| 113 | 100 | 80 | none |
| 114 | 100 | 93 | none |
| 115 | 100 | 100 | none |
| 116 | 100 | 74 | none |
| 117 | 100 | 85 | none |
| 118 | 100 | 100 | none |
| 119 | 100 | 95 | none |
| 120 | 100 | 83 | none |
| 121 | 100 | 78 | none |
| 122 | 100 | 93 | none |
| 123 | 100 | 88 | none |
| 124 | 100 | 90 | none |
| 125 | 100 | 95 | none |
| 126 | 100 | 100 | none |
| 127 | 100 | 82 | none |
| 128 | 100 | 75 | none |
| 129 | 100 | 86 | none |
| 130 | 100 | 96 | none |
| 131 | 100 | 100 | none |
| 132 | 100 | 68 | none |
| 133 | 100 | 100 | none |
| 134 | 100 | 80 | none |
| 135 | 100 | 93 | none |
| 136 | 100 | 100 | none |
| 137 | 100 | 98 | none |
| 138 | 100 | 75 | none |
| 139 | 100 | 90 | none |
| 140 | 100 | 92 | none |
| 141 | 100 | 90 | none |
| 142 | 100 | 88 | none |
| 143 | 100 | 80 | none |
| 144 | 100 | 74 | none |
| 145 | 100 | 75 | none |
| 146 | 100 | 70 | none |
| 147 | 100 | 86 | none |
| 148 | 100 | 80 | none |
| 149 | 100 | 83 | none |
| 150 | 100 | 100 | none |
| 151 | 100 | 89 | none |
| 152 | 100 | 80 | none |
| 157 | 100 | 70 | none |
| 158 | 100 | 90 | none |
| 159 | 100 | 90 | none |

TABLE 10-continued

| Compound No. | Concentration (ppm) | Control effect (%) | Phytotoxicity |
|---|---|---|---|
| 161 | 100 | 95 | none |
| 162 | 100 | 90 | none |
| 163 | 100 | 74 | none |
| 164 | 100 | 70 | none |
| 168 | 100 | 70 | none |
| 169 | 100 | 75 | none |
| 170 | 100 | 90 | none |
| 171 | 100 | 86 | none |
| 172 | 100 | 80 | none |
| 173 | 100 | 72 | none |
| 174 | 100 | 88 | none |
| 175 | 100 | 92 | none |
| 176 | 100 | 90 | none |
| 177 | 100 | 100 | none |
| 178 | 100 | 92 | none |

We claim:

1. An imidazol-1-yl-carboxylic acid ester derivative represented by the formula

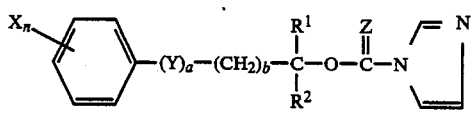

wherein $R^1$ is lower alkyl, $C_{3-8}$ cycloalkyl, or $R^3(CH_3)_2C-$ (wherein $R^3$ is halogenomethyl, acetyloxymethyl, propionyloxymethyl, benzoyloxymethyl optionally having a halogen atom, $C_{1-3}$ alkyl or $C_{1-3}$ alkoxy on the phenyl ring, or lower alkoxycarbonyl), $R^2$ is a hydrogen atom, lower alkyl or $C_{3-8}$ cycloalkyl, X is a hydrogen atom, halogen atom, lower alkyl, $C_{3-8}$ cycloalkyl, lower alkenyl, lower alkoxy, lower alkenyloxy, lower alkynyloxy, lower alkylthio, $C_{1-6}$ haloalkyl, $C_{2-6}$ haloalkenyl, substituted or unsubstituted phenyl, substituted or unsubstituted benzyl, substituted or unsubstituted phenoxy (wherein the substituents on the phenyl ring of phenyl, benzyl and phenoxy are selected from the group consisting of halogen atom, lower alkyl, lower alkoxy, nitro and cyano), nitro, cyano, $-COR^4$ (wherein $R^4$ is lower alkoxy, lower alkenyloxy, benzyloxy, lower alkylamino or anilino) or

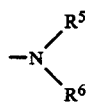

(wherein $R^5$ and $R^6$ are each lower alkyl, acetyl, propionyl, benzoyl optionally having a halogen atom, $C_{1-3}$ alkyl or $C_{1-3}$ alkoxy on the phenyl ring, methylsulfonyl, ethylsulfonyl, benzensulfonyl optionally substituted with a halogen atom, $C_{1-3}$ alkyl or $C_{1-3}$ alkoxy on the phenyl ring, or lower alkoxycarbonyl), n is an integer of from 1 to 3, Y and Z are the same or different and are each an oxygen atom or sulfur atom, a is 0 or 1, and b is 1 or 2.

2. An imidazol-1-yl-carboxylic acid ester derivative represented by the formula

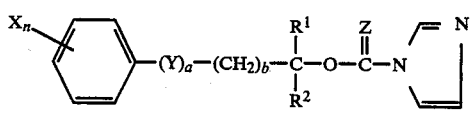

wherein $R^1$ is lower alkyl, $C_{3-8}$ cycloalkyl, or $R^3(CH_3)_2C-$ (wherein $R^3$ is halogenomethyl, acetyloxymethyl, propionyloxymethyl, benzoyloxymethyl optionally having a halogen atom, $C_{1-3}$ alkyl or $C_{1-3}$ alkoxy on the phenyl ring, or lower alkoxycarbonyl), $R^2$ is a hydrogen atom, lower alkyl or $C_{3-8}$ cycloalkyl, X is a hydrogen atom, halogen atom, lower alkyl, $C_{3-8}$ cycloalkyl, lower alkenyl, lower alkoxy, lower alkenyloxy, lower alkynyloxy, lower alkylthio, $C_{1-6}$ haloalkyl, $C_{2-6}$ haloalkenyl, substituted or unsubstituted phenyl, substituted or unsubstituted benzyl, substituted or unsubstituted phenoxy (wherein the substituents on the phenyl ring of phenyl, benzyl and phenoxy are selected from the group consisting of halogen atom, lower alkyl, lower alkoxy, nitro and cyano), nitro, cyano, $-COR^4$ (wherein $R^4$ is lower alkoxy, lower alkenyloxy, benzyloxy, lower alkylamino or anilino) or

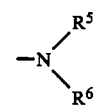

(wherein $R^5$ and $R^6$ are each lower alkyl, acetyl, propionyl, benzoyl optionally having a halogen atom, $C_{1-3}$ alkyl or $C_{1-3}$ alkoxy on the phenyl ring, methylsulfonyl, ethylsulfonyl, benzensulfonyl optionally substituted with a halogen atom, $C_{1-3}$ alkyl or $C_{1-3}$ alkoxy on the phenyl ring, or lower alkoxycarbonyl, or one of $R^5$ and $R^6$ is a hydrogen atom and the other is lower alkoxycarbonyl, acetyl, propionyl, benzoyl, methylsulfonyl or toluene sulfonyl), n is an integer of from 1 to 3, Y and Z are the same or different and are each an oxygen atom or sulfur atom, a is 0 or 1, and b is 1 or 2.

3. An imidazole-1-yl-carboxylic acid ester derivative as defined in claim 2 which is represented by the formula

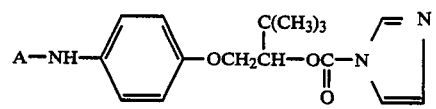

wherein A is methoxycarbonyl, iso-propyloxycarbonyl, n-butoxycarbonyl, acetyl, propionyl, benzoyl, methylsulfonyl or toluene sulfonyl.

4. An imidazole-1-yl-carboxylic acid ester derivative as defined in claim 2 which is represented by the formula

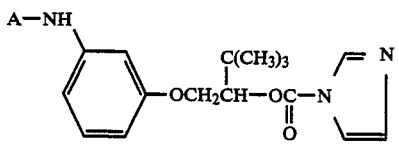

wherein A is ethoxycarbonyl, propionyl or methylsulfonyl.

5. A fungicidal composition comprising a fungicidally effective amount of an active component and a carrier, the active component being an imidazol-1-yl-carboxylic acid ester derivative represented by the formula

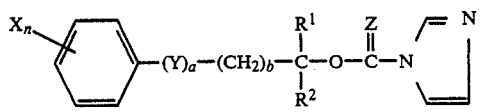

wherein $R^1$ is lower alkyl, $C_{3-8}$ cycloalkyl, or $R^3(CH_3)_2C-$ (wherein $R^3$ is halogenomethyl, acetyloxymethyl, propionyloxymethyl, benzoyloxymethyl optionally having a halogen atom, $C_{1-3}$ alkyl or $C_{1-3}$ alkoxy on the phenyl ring, or lower alkoxycarbonyl), $R^2$ is a hydrogen atom, lower alkyl or $C_{3-8}$ cycloalkyl, X is a hydrogen atom, halogen atom, lower alkyl, $C_{3-8}$ cycloalkyl, lower alkenyl, lower alkoxy, lower alkenyloxy, lower alkynyloxy, lower alkylthio, $C_{1-6}$ haloalkyl, $C_{2-6}$ haloalkenyl, substituted or unsubstituted phenyl, substituted or unsubstituted benzyl, substituted or unsubstituted phenoxy (wherein the substituents on the phenyl ring of phenyl, benzyl and phenoxy are selected from the group consisting of halogen atom, lower alkyl, lower alkoxy, nitro and cyano), nitro, cyano, $-COR^4$ (wherein $R^4$ is lower alkoxy, lower alkenyloxy, benzyloxy, lower alkylamino or anilino) or

(wherein $R^5$ and $R^6$ are each lower alkyl, acetyl, propionyl, benzoyl optionally having a halogen atom, $C_{1-3}$ alkyl or $C_{1-3}$ alkoxy on the phenyl ring, methylsulfonyl, ethylsulfonyl, benzensulfonyl optionally substituted with a halogen atom, $C_{1-3}$ alkyl or $C_{1-3}$ alkoxy on the phenyl ring, or lower alkoxycarbonyl), n is an integer of from 1 to 3, Y and Z are the same or different and are each an oxygen atom or sulfur atom, a is 0 or 1, and b is 1 or 2.

6. A fungicidal composition comprising a fungicidally effective amount of an active component and a carrier, the active component being an imidazolo-1-yl-carboxylic acid ester derivative represented by the formula

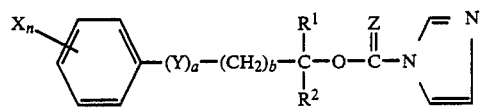

wherein $R^1$ is lower alkyl, $C_{3-8}$ cycloalkyl, or $R^3(CH_3)_2C-$ (wherein $R^3$ is halogenomethyl, acetyloxymethyl, propionyloxymethyl, benzoyloxymethyl optionally having a halogen atom, $C_{1-3}$ alkyl or $C_{1-3}$ alkoxy on the phenyl ring, or lower alkoxycarbonyl), $R^2$ is a hydrogen atom, lower alkyl or $C_{3-8}$ cycloalkyl, X is a hydrogen atom, halogen atom, lower alkyl, $C_{3-8}$ cycloalkyl, lower alkenyl, lower alkoxy, lower alkenyloxy, lower alkynyloxy, lower alkylthio, $C_{1-6}$ haloalkyl, $C_{2-6}$ haloalkenyl, substituted or unsubstituted phenyl, substituted or unsubstituted benzyl, substituted or unsubstituted phenoxy (wherein the substituents on the phenyl ring of phenyl, benzyl and phenoxy are selected from the group consisting of halogen atom, lower alkyl, lower alkoxy, nitro and cyano), nitro, cyano, $-COR^4$ (wherein $R^4$ is lower alkoxy, lower alkenyloxy, benzyloxy, lower alkylamino or anilino) or

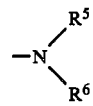

(wherein $R^5$ and $R^6$ are each lower alkyl, acetyl, propionyl, benzoyl optionally having a halogen atom, $C_{1-3}$ alkyl or $C_{1-3}$ alkoxy on the phenyl ring, methylsulfonyl, ethylsulfonyl, benzensulfonyl optionally substituted with a halogen atom, $C_{1-3}$ alkyl or $C_{1-3}$ alkoxy on the phenyl ring, or lower alkoxycarbonyl, or one of $R^5$ and $R^6$ is a hydrogen atom and the other is lower alkoxycarbonyl, acetyl, propionyl, benzoyl, methylsulfonyl or toluene sulfonyl), n is an integer of from 1 to 3, Y and Z are the same or different and are each an oxygen atom or sulfur atom, a is 0 or 1, and b is 1 or 2.

7. A fungicidal composition as defined in claim 5 containing 0.1 to 90% by weight of the active component.

8. A fungicidal composition as defined in claim 6 containing 0.1 to 90% by weight of the active component.

* * * * *